(12) United States Patent
Abdur-Rashid et al.

(10) Patent No.: US 9,062,085 B2
(45) Date of Patent: Jun. 23, 2015

(54) BIARYL DIPHOSPHINE LIGANDS, INTERMEDIATES OF THE SAME AND THEIR USE IN ASYMMETRIC CATALYSIS

(75) Inventors: Kamaluddin Abdur-Rashid, Mississauga (CA); Wenli Jia, Toronto (CA); Shuiming Lu, Toronto (CA); Rongwei Guo, Oakville (CA); Xuanhua Chen, Oakville (CA); Dino Amoroso, Binbrook (CA)

(73) Assignee: Kanata Chemical Technologies Inc., Toronto, Ontario (CA)

( * ) Notice: Subject to any disclaimer, the term of this patent is extended or adjusted under 35 U.S.C. 154(b) by 187 days.

(21) Appl. No.: 13/821,290

(22) PCT Filed: Sep. 9, 2011

(86) PCT No.: PCT/CA2011/001024
§ 371 (c)(1),
(2), (4) Date: Mar. 7, 2013

(87) PCT Pub. No.: WO2012/031358
PCT Pub. Date: Mar. 15, 2012

(65) Prior Publication Data
US 2013/0184479 A1 Jul. 18, 2013

Related U.S. Application Data

(60) Provisional application No. 61/381,493, filed on Sep. 10, 2010.

(51) Int. Cl.
*C07F 15/00* (2006.01)
*C07F 9/46* (2006.01)
(Continued)

(52) U.S. Cl.
CPC .......... *C07F 15/0093* (2013.01); *C07B 53/00* (2013.01); *C07B 2200/07* (2013.01);
(Continued)

(58) Field of Classification Search
CPC .......... C07F 15/0093; C07F 15/0066; C07F 15/008; C07F 15/0053; C07F 9/46; C07F 9/5325; C07F 9/5329; C07F 9/4021

USPC ................. 556/19; 558/162; 568/13
See application file for complete search history.

(56) References Cited

U.S. PATENT DOCUMENTS 5,302,738 A 4/1994 Foricher et al.
5,488,172 A 1/1996 Cereghetti et al.
(Continued)

OTHER PUBLICATIONS

Schmid R. et al. Helvetica Chimica Acta. 74:370-389, 1991.
(Continued)

*Primary Examiner* — Porfirio Nazario Gonzalez
(74) *Attorney, Agent, or Firm* — Bereskin & Parr LLP/S.E.N.C.R.L.. s.r.l.; Michael Fenwick

(57) ABSTRACT

The present disclosure relates to biaryl diphosphine ligands of the formula (B), processes for the production of the ligands and the use of the ligands in metal catalysts for asymmetric synthesis. The disclosure also relates to intermediates used for the production of the biaryl diphosphine ligand. (Formula (B))

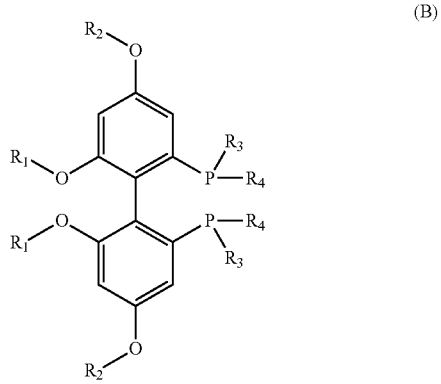

19 Claims, 1 Drawing Sheet

(51) Int. Cl.

| | |
|---|---|
| *C07B 53/00* | (2006.01) |
| *C07C 29/145* | (2006.01) |
| *C07C 67/31* | (2006.01) |
| *C07D 333/22* | (2006.01) |
| *C07F 9/40* | (2006.01) |
| *C07F 9/42* | (2006.01) |
| *C07F 9/50* | (2006.01) |
| *C07F 9/53* | (2006.01) |

(52) U.S. Cl.
CPC ........... *C07C29/145* (2013.01); *C07C 67/31* (2013.01); *C07D 333/22* (2013.01); *C07F 9/4021* (2013.01); *C07F 9/4025* (2013.01); *C07F 9/42* (2013.01); *C07F 9/5027* (2013.01); *C07F 9/5325* (2013.01); *C07F 9/5329* (2013.01); *C07F 15/0053* (2013.01); *C07F 15/0066* (2013.01); *C07F 9/46* (2013.01)

(56) References Cited

U.S. PATENT DOCUMENTS

| | | |
|---|---|---|
| 6,162,929 A | 12/2000 | Foricher et al. |
| 2002/0035271 A1 | 3/2002 | Sirges et al. |

OTHER PUBLICATIONS

Wu, Jing et al, Tetrahedron Letters. 43:1539-1543, 2002.
R. Noyori et al. Acc. Chem. Res. 1990, 23(10), 345-350.
M.J. Burk et al. Organometallics 1990, 9(10), 2653-2655.
T. Saito et al. Adv. Synth. Catal. 2001, 343(3), 264-267.
B. Heiser et al. Tetrahedron: Asymmetry 1991, 2(1), 51-62.
J.P. Henschke et al. Adv. Synth. Catal. 2003, 345(1+2), 300-307.
A.S.C. Chan et al. J. Am. Chem. Soc. 2000, 122(46), 11413-11514.
Gorobets, E. et al. Synthesis, resolution and applications of 3,3'-bis(RO)-MeO-BIPHEP derivatives. Tetrahedron Letters. 45:3597-3601, 2004.
Gorobets, E. et al. Diaterospecific Intramolecular Ullmann Couplings: Unique Chiral Auxiliary for the Preparation of 3,3'-Disubstituted MeO-BIPHEP derivatives. Organic Letters. 8(7):1483-1485, 2006.
Ma, Meng Lin et al. Alkoxy substituted MeO-BIPHEP-type diphosphines ligands for asymmetric hydrogenation of aryl ketones. Chinese Chemical Letters 21:576-579, 2010.
Nelson, Todd D. et al. Cu, Ni and Pd Mediated Homocoupling Reactions in Biaryl Synthesis: The Ullmann Reaction. Organic Reactions. 63:265, 2004.
Shimizu, Hideo et al. Recent advances in biaryl-type bisphosphine ligands. Tetrahedron. 61:5405-5432, 2005.
Tang, Wenjun et al. New Chiral Phosphorus Ligands for Enanioselective Hydrogenation. Chem. Rev. 103:3029-3069, 2003.
Wu, J. et al. Air-Stable Catalysts for Highly Efficient and Enanioselective Hydrogenation of Aromatic Ketones. Supporting Information 1. S1-S3, (2002).
Wu, J. et al. Air-Stable Catalysts for Highly Efficient and Enanioselective Hydrogenation of Aromatic Ketones. J. Org. Chem. 67:7908-7910, 2002.

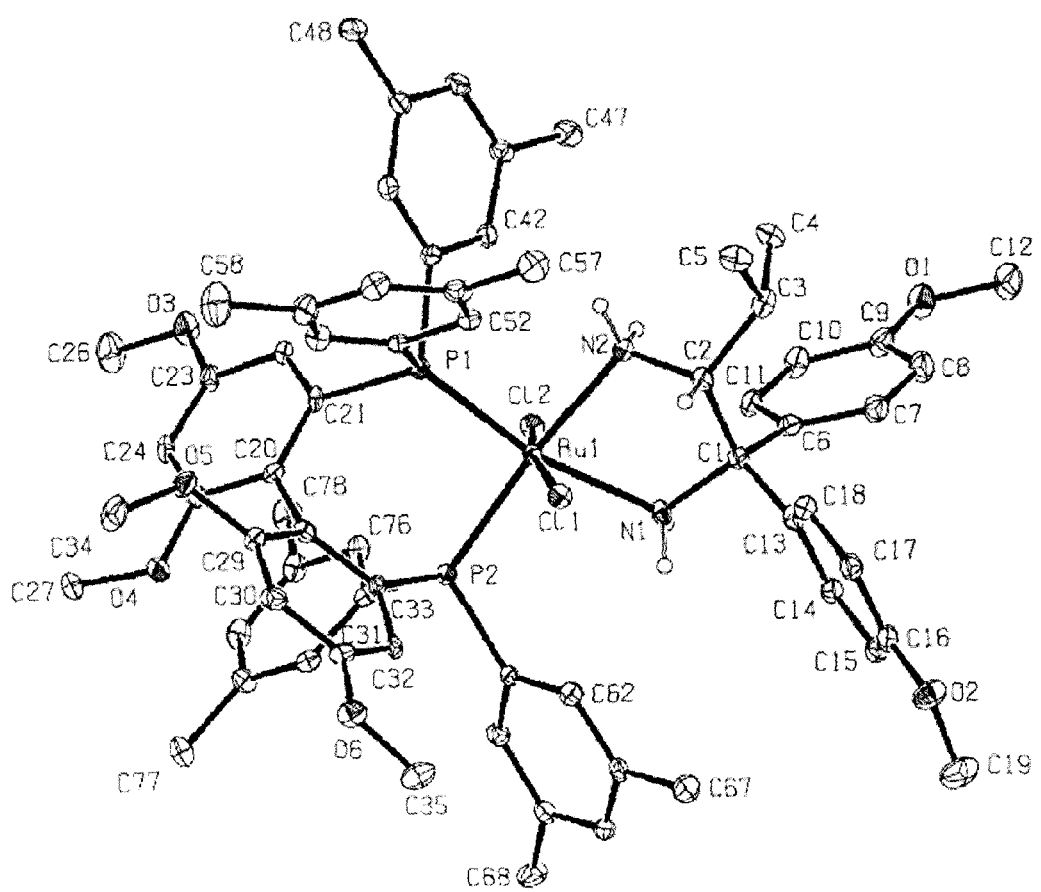

BIARYL DIPHOSPHINE LIGANDS, INTERMEDIATES OF THE SAME AND THEIR USE IN ASYMMETRIC CATALYSIS

CROSS REFERENCE TO RELATED APPLICATIONS

This is a national stage application of PCT/CA2011/001024, filed Sep. 9, 2011, which claims priority from U.S. Provisional patent application Ser. No. 61/381,493 filed Sep. 10, 2010, all of which are incorporated herein by reference in their entirety.

FIELD OF THE DISCLOSURE

The present disclosure relates to biaryl diphosphine ligands, processes for the production of the ligands and the use of the ligands in metal catalysts for asymmetric synthesis. The disclosure also relates to intermediates used for the production of the biaryl diphosphine ligands.

BACKGROUND OF THE DISCLOSURE

There are numerous reports relating to transition metal complexes that are used for asymmetric synthesis, including hydrogenations, transfer hydrogenations, isomerizations, oxidations, hydrosilylations, hydroborations, coupling reactions, amongst others. The reactions are usually mediated by transition metal complexes in which metals such as ruthenium, rhodium, iridium, palladium, etc. are coordinated with a tertiary phosphine compound as a catalyst.

Numerous chiral diphosphine compounds having various structures have been developed. These include Binap (R. Noyori et al. *Acc. Chem. Res.* 1990, 23(10), 345-350), Duphos and BPE (M. J. Burk et al. *Organometallics* 1990, 9(10), 2653-2655), Segphos (T. Saito et al. *Adv. Synth. Catal.* 2001, 343(3), 264-267), Biphemp (B. Heiser et al. *Tetrahedron: Asymmetry* 1991, 2(1), 51-62), Hexaphemp (J. P. Henschke et al. *Adv. Synth. Catal.* 2003, 345(1+2), 300-307), P-Phos (A. S. C. Chan et al. *J. Am. Chem. Soc.* 2000, 122(46), 11413-11514), MeO-Biphep (R. Schmid et al. *Helv. Chim. Acta* 1991, 74(2), 370-389), among others. In the subclass of biaryl diphosphine ligands, it has been shown that incorporation of small substituents such as methyl and methoxy groups at the b- and 6'-positions confer atropisomerism. Variations of these biaryl diphosphines containing alkoxy substituents include (R)- and (S)-(6,6'-dimethoxy(1,1-diphenyl)-2,2'-diyl)bis(diarylphosphine), or (R)- and (S)-(5,5',6,6'-tetramethoxy(1,1'-diphenyl)-2,2'-diyl)bis(diarylphosphine), or (R)- and (S)-(4,4',5,5',6,6'-hexamethoxy(1,1'-diphenyl)-2,2'-diyl)bis(diarylphosphine) (R. Schmid et al. *Helv. Chim. Acta* 1991, 74(2), 370-389).

The preparation of the biaryl diphosphine ligands of the prior art are based on copper catalyzed Ullmann coupling of holophosphonate intermediates of formulae II, III and IV, which were subsequently reduced to the respective biaryl diphospines (R. Schmid et al. *Helv. Chim. Acta* 1991, 74(2), 370-389).

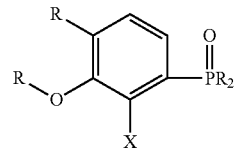

II

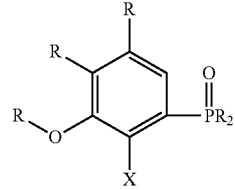

III

IV

Intermediates II, III and IV were prepared by the ortholithiation of precursors of formulae V, VI and VII followed by halogenation with molecular I₂, Br₂, ICl or IBr (R. Schmid et al. *Helv. Chim. Acta* 1991, 74(2), 370-389).

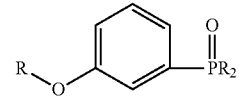

V

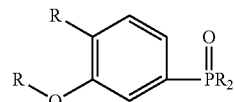

VI

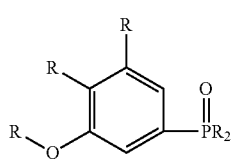

VII

For applications in industrial asymmetric catalysis, a metal catalyst comprising a transition metal complex of a chiral ligand must exhibit high activity and enantioselectivity for the desired transformation of a particular substrate. It is also equally important that the chiral ligand and its precursors can be prepared efficiently by an optimized synthetic route that is also amenable to scale-up. Although a very large number of chiral diphosphine ligands have been prepared in research quantities, only relatively few have been developed commercially. Hence, synthetic accessibility can often be the limiting factor for various diphosphine ligands reported in the literature.

SUMMARY OF THE DISCLOSURE

The phosphine compounds (1) which can be used in an Ullmann coupling to produce the biaryl disphosphine ligands compounds (2) have not been prepared or isolated.

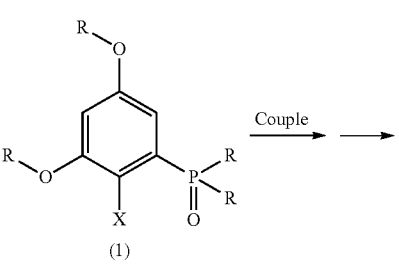

(1)

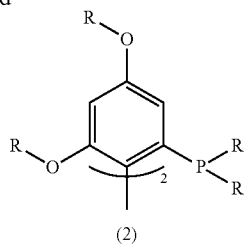

(2)

Without being bound by theory, it is thought that the 6,6'-alkoxy groups of (2) imparts atropisomerism in the molecule, while the 4,4'-alkoxy groups facilitate enhanced stereoselectivity and activity of catalysts derived from these compounds. Attempts to develop a viable method to prepare compounds of the formula (1) starting with compounds of formula (3) using ortholithiation and halogenation procedures described in the prior art have been unsuccessful due to the ortho-directing power of the alkoxy groups, resulting in polyhalogenated species, such as (4).

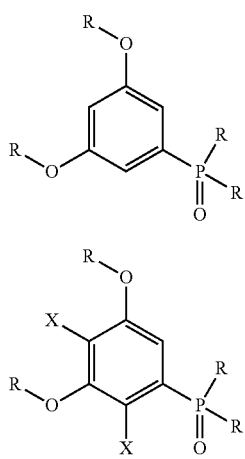

(3)

(4)

Accordingly, the present disclosure relates to intermediates which can be used for the production of biaryl diphosphine ligands, wherein the intermediate is a compound of the Formula A

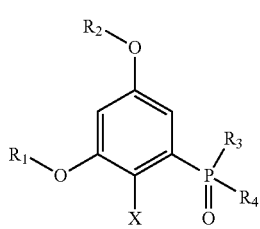

(A)

wherein $R_1$ and $R_2$ are independently or simultaneously $C_{1-20}$-(alkyl), $C_{2-20}$-(alkenyl), $C_{2-20}$-(alkynyl), $C_{3-20}$-(cycloalkyl) or $C_{6-14}$-(aryl), all of which are optionally substituted, $R_3$ and $R_4$ are independently or simultaneously $C_{1-20}$-(alkyl), $C_{2-20}$-(alkenyl), $C_{2-20}$-(alkynyl), $C_{3-20}$-(cycloalkyl), $C_{6-14}$-(aryl), $C_{5-14}$-(heteroaryl)-O—$C_{1-20}$-(alkyl), —O—$C_{6-14}$-(aryl), —O—$CH_2$—$C_{6-14}$-(aryl), all of which are optionally substituted, or $R^3$ and $R^4$ are linked together to form an optionally substituted monocyclic or polycylic ring system having 4 or more atoms, including the phosphorous atom to which said groups are bonded, and in which one or more carbon atoms in said monocyclic or polycyclic ring system is optionally replaced with a heteromoiety selected from O, S, N, $NR^5$, $SiR^5$ and $SiR^5R^6$, the optional substituents are selected from one or more of halo, $OR^5$, $NR^5R^6$ and $R^7$, $R^5$ and $R^6$ are simultaneously or independently H, fluoro-substituted-$C_{1-6}$alkyl, $C_{1-6}$alkyl, $C_{2-6}$alkenyl, $C_{2-6}$alkynyl or $C_{6-14}$aryl, $R^7$ is fluoro-substituted-$C_{1-6}$alkyl, $C_{1-6}$alkyl, $C_{2-6}$alkenyl, $C_{2-6}$alkynyl, or $C_{6-14}$aryl, and X is halo.

Also included in the present disclosure are biaryl diphosphine ligands of the Formula (B)

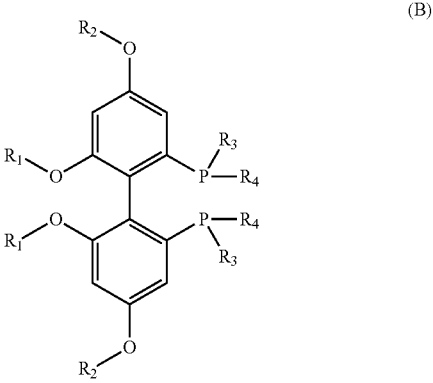

(B)

wherein $R_1$ and $R_2$ are independently or simultaneously $C_{1-20}$-(alkyl), $C_{2-20}$-(alkenyl), $C_{2-20}$-(alkynyl), $C_{3-20}$-(cycloalkyl) or $C_{6-14}$-(aryl), all of which are optionally substituted, $R_3$ and $R_4$ are independently or simultaneously $C_{1-20}$-(alkyl), $C_{2-20}$-(alkenyl), $C_{2-20}$-(alkynyl), $C_{3-20}$-(cycloalkyl), $C_{6-14}$-(aryl), $C_{6-14}$-(heteroaryl)-O—$C_{1-20}$-(alkyl), —O—$C_{6-14}$-(aryl), —O—$CH_2$—$C_{6-14}$-(aryl), all of which are optionally substituted, or $R^3$ and $R^4$ are linked together to form an optionally substituted monocyclic or polycylic ring system having 4 or more atoms, including the phosphorous atom to which said groups are bonded, and in which one or more carbon atoms in said monocyclic or polycyclic ring system is optionally replaced with a heteromoiety selected from O, S, N, $NR^5$, $SiR^5$ and $SiR^5R^6$, the optional substituents are selected from one or more of halo, $OR^5$, $NR^5R^6$ and $R^7$, $R^5$ and $R^6$ are simultaneously or independently H, fluoro-substituted-$C_{1-6}$alkyl, $C_{1-6}$alkyl, $C_{2-6}$alkenyl, $C_{2-6}$alkynyl or $C_{6-14}$aryl, and $R^7$ is fluoro-substituted-$C_{1-6}$alkyl, $C_{1-6}$alkyl, $C_{2-6}$alkenyl, $C_{2-6}$alkynyl, or $C_{6-14}$aryl.

The transformations to which the compounds of the disclosure can be applied include but are not limited to: hydrogenation, transfer hydrogenation, hydroformylation, hydrosilylation, hydroboration, hydroamination, hydrovinylation, hydroarylation, hydration, oxidation, epoxidation, reduction, C—C and C—X bond formation (includes things like Heck, Suzuki-Miyaura, Negishi, Buchwald-Hartwig Amination, α-Ketone Arylation, N-Aryl Amination, Murahashi, Kumada, Negishi and Stille reactions etc.), functional group interconversion, kinetic resolution, dynamic kinetic resolution, cycloaddition, Diels-Alder reactions, retro-Diels-Alder reactions, sigmatropic rearrangements, electrocyclic reactions, ring-opening, ring-closing, olefin metathesis, carbonylation, and aziridination. In all transformations listed above the reactions may or may not be regioselective, chemoselective, stereoselective or diastereoselective.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in greater detail with reference to the following drawings in which:

FIG. 1 shows an x-ray crystallographic structure of a metal complex containing a compound of the formula (B) in an embodiment of the present disclosure.

DETAILED DESCRIPTION OF THE DISCLOSURE (I) Definitions

The term "$C_{1-n}$-(alkyl)" as used herein means straight and/or branched chain, saturated alkyl radicals containing from one to "n" carbon atoms and includes (depending on the identity of n) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable n is an integer representing the largest number of carbon atoms in the alkyl radical.

The term "$C_{1-n}$-(alkenyl)" as used herein means straight and/or branched chain, unsaturated alkyl radicals containing from one to n carbon atoms and one to three double bonds, and includes (depending on the identity of n) vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like, where the variable n is an integer representing the largest number of carbon atoms in the alkenyl radical.

The term "$C_{1-n}$-(alkynyl)" as used herein means straight and/or branched chain, unsaturated alkyl radicals containing from one to n carbon atoms and one to three triple bonds, and includes (depending on the identity of n) acetylynyl, propynyl, but-1-ynyl, but-2-ynyl, but-3-ynyl, 3-methylbut-1-enyl, 3-methylpent-1-ynyl, 4-methylpent-1-ynyl, 4-methylpent-2-ynyl, penta-1,3-di-ynyl, hexyn-1-yl and the like, where the variable n is an integer representing the largest number of carbon atoms in the alkynyl radical.

The term "$C_{3-n}$-(cycloalkyl)" as used herein means a monocyclic, bicyclic or tricyclic saturated carbocylic group containing from three to n carbon atoms and includes (depending on the identity of n) cyclopropyl, cyclobutyl, cyclopentyl, cyclodecyl and the like.

The term "aryl" as used herein means a monocyclic, bicyclic or tricyclic aromatic ring system containing at least one aromatic ring and from 6 to 14 carbon atoms and includes phenyl, naphthyl, anthracenyl, 1,2-dihydronaphthyl, 1,2,3,4-tetrahydronaphthyl, fluorenyl, indanyl, indenyl and the like.

The term "heteroaryl" as used herein means a monocyclic, bicyclic or tricyclic ring system containing one or two aromatic rings and from 5 to 14 atoms of which, unless otherwise specified, one, two, three, four or five are heteromoieties independently selected from N, NH, N($C_{1-6}$alkyl), O and S and includes thienyl, furyl, pyrrolyl, pyrididyl, indolyl, quinolyl, isoquinolyl, tetrahydroquinolyl, benzofuryl, benzothienyl and the like.

The term "halo" as used herein means halogen and includes chloro, fluoro, bromo or iodo.

The term "fluoro-substituted" as used herein means that at least one, including all, of the hydrogens on the referenced group is replaced with fluorine.

The suffix "ene" added on to any of the above groups means that the group is divalent, i.e. inserted between two other groups.

The term "ring system" as used herein refers to a carbon-containing ring system, that includes monocycles, fused bicyclic and polycyclic rings, bridged rings and metalocenes. Where specified, the carbons in the rings may be substituted or replaced with heteroatoms.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

(II) Compounds of the Disclosure

The present disclosure relates to intermediate mono-phosphine compounds which can be used to produce biaryl diphosphine ligands, which are useful in metal catalysis. Accordingly, in an embodiment of the disclosure, there is provided a compound of the Formula A:

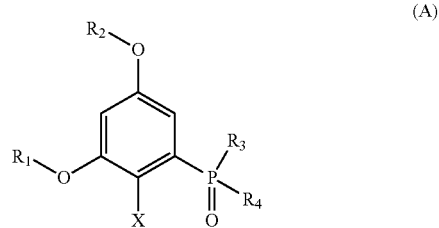

(A)

wherein $R_1$ and $R_2$ are independently or simultaneously $C_{1-20}$-(alkyl), $C_{2-20}$-(alkenyl), $C_{2-20}$-(alkynyl), $C_{3-20}$-(cycloalkyl) or $C_{6-14}$-(aryl), all of which are optionally substituted, $R_3$ and $R_4$ are independently or simultaneously $C_{1-20}$-(alkyl), $C_{2-20}$-(alkenyl), $C_{2-20}$-(alkynyl), $C_{3-20}$-(cycloalkyl), $C_{6-14}$-(aryl), $C_{5-14}$-(heteroaryl)-O—$C_{1-20}$-(alkyl), —O—$C_{6-14}$-(aryl), —O—$CH_2$—$C_{6-14}$-(aryl), all of which are optionally substituted, or $R^3$ and $R^4$ are linked together to form an optionally substituted monocyclic or polycylic ring system having 4 or more atoms, including the phosphorous atom to which said groups are bonded, and in which one or more carbon atoms in said monocyclic or polycyclic ring system is optionally replaced with a heteromoiety selected from O, S, N, $NR^5$, $SiR^5$ and $SiR^5R^6$, the optional substituents are selected from one or more of halo, $OR^5$, $NR^5R^6$ and $R^7$, $R^5$ and $R^6$ are simultaneously or independently H, fluoro-substituted-$C_{1-6}$alkyl, $C_{1-6}$alkyl, $C_{2-6}$alkenyl, $C_{2-6}$alkynyl or $C_{6-14}$aryl, $R^7$ is fluoro-substituted-$C_{1-6}$alkyl, $C_{1-6}$alkyl, $C_{2-6}$alkenyl, $C_{2-6}$alkynyl, or $C_{6-14}$aryl, and X is halo.

In a further embodiment, $R_1$ and $R_2$ are independently or simultaneously $C_{1-10}$-(alkyl), $C_{2-10}$-(alkenyl), $C_{2-10}$-(alkynyl), $C_{3-10}$-(cycloalkyl) or $C_{6-10}$-(aryl), all of which are optionally substituted. In another embodiment, $R_1$ and $R_2$ are independently or simultaneously $C_{1-6}$-(alkyl), $C_{2-6}$-(alkenyl), $C_{2-6}$-(alkynyl), $C_{3-6}$-(cycioalkyl) or phenyl, all of which are optionally substituted. In another embodiment, $R_1$ and $R_2$ are independently or simultaneously methyl, ethyl, propyl, butyl or phenyl, all of which are optionally substituted. In a further embodiment, $R_1$ and $R_2$ are independently or simultaneously methyl, ethyl or propyl, all of which are optionally substituted. In a further embodiment, $R_1$ and $R_2$ are methyl.

In another embodiment of the disclosure, $R_3$ and $R_4$ are independently or simultaneously $C_{1-10}$-(alkyl), $C_{2-10}$-(alkenyl), $C_{2-10}$-(alkynyl), $C_{3-10}$-(cycloalkyl), $C_{6-10}$-(aryl), $C_{6-10}$-(heteroaryl)-O—$C_{1-10}$-(alkyl), —O—$C_{6-10}$-(aryl), —O—$CH_2$—$C_{6-10}$-(aryl), all of which are optionally substituted. In another embodiment, $R_3$ and $R_4$ are independently or simultaneously $C_{1-6}$-(alkyl), $C_{2-6}$-(alkenyl), $C_{2-6}$-(alkynyl), $C_{3-6}$-(cycloalkyl), phenyl, $C_{5-6}$-(heteroaryl)-O—$C_{1-6}$-(alkyl), —O-phenyl, —O—$CH_2$-phenyl, all of which are optionally substituted. In another embodiment, $R_3$ and $R_4$ are independently or simultaneously phenyl, tolyl (4-methylphenyl), anisyl (4-methoxyphenyl), xylyl (3,5-dimethylphenyl), 3,5-dimethyl-4-methoxy-phenyl, 3,5-di-tert-butyl-4-methoxy-phenyl or 3,5-bis(trifluoromethyl)-phenyl, all of which are optionally substituted.

In another embodiment, $R^3$ and $R^4$ are linked together to form an optionally substituted monocyclic or bicyclic, saturated, unsaturated and/or aromatic ring system having 4 to 14 atoms, including the phosphorous atom to which said groups are bonded, and in which one or more carbon atoms in said monocyclic or bicyclic ring system is optionally replaced with a heteromoiety selected from O, S, N, NH and $NC_{1-4}$alkyl. In a further embodiment, $R^3$ and $R^4$ are linked together to form an optionally substituted monocyclic or bicyclic, saturated, unsaturated and/or aromatic ring system having 4 to 10 atoms, including the phosphorous atom to which said groups are bonded.

In another embodiment, the optional substituents are one or more of halo, OH, $NH_2$, $NHR^5$, $OR^5$, $NR^5R^6$ and $R^7$, in which $R^5$, $R^6$ and $R^7$ are simultaneously or independently selected from fluoro-substituted-$C_{1-4}$alkyl, $C_{1-4}$alkyl, $C_{2-4}$alkenyl, phenyl and $C_{1-4}$alkylenephenyl, specifically methyl, benzyl and phenyl.

In another embodiment, X is F, Cl, Br or I. In another embodiment, X is Cl or Br.

In another embodiment of the disclosure, there is also provided a compound of the Formula B

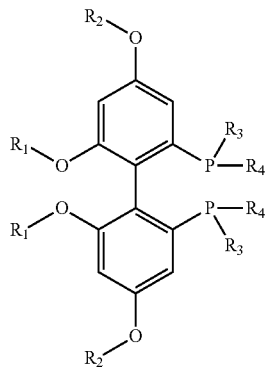

(B)

wherein $R_1$ and $R_2$ are independently or simultaneously $C_{1-20}$-(alkyl), $C_{2-20}$-(alkenyl), $C_{2-20}$-(alkynyl), $C_{3-20}$-(cycloalkyl) or $C_{6-14}$-(aryl), all of which are optionally substituted, $R_3$ and $R_4$ are independently or simultaneously $C_{1-20}$-(alkyl), $C_{2-20}$-(alkenyl), $C_{2-20}$-(alkynyl), $C_{3-20}$-(cycloalkyl), $C_{6-14}$-(aryl), $C_{6-14}$-(heteroaryl)-O—$C_{1-20}$-(alkyl), —O—$C_{6-14}$-(aryl), —O—$CH_2$—$C_{6-14}$-(aryl), all of which are optionally substituted, or $R^3$ and $R^4$ are linked together to form an optionally substituted monocyclic or polycylic ring system having 4 or more atoms, including the phosphorous atom to which said groups are bonded, and in which one or more carbon atoms in said monocyclic or polycyclic ring system is optionally replaced with a heteromoiety selected from O, S, N, $NR^5$, $SiR^5$ and $SiR^5R^6$, the optional substituents are selected from one or more of halo, $OR^5$, $NR^5R^6$ and $R^7$, $R^5$ and $R^6$ are simultaneously or independently H, fluoro-substituted-$C_{1-6}$alkyl, $C_{1-6}$alkyl, $C_{2-6}$alkenyl, $C_{2-6}$alkynyl or $C_{6-14}$aryl, and $R^7$ is fluoro-substituted-$C_{1-6}$alkyl, $C_{1-6}$alkyl, $C_{2-6}$alkenyl, $C_{2-6}$alkynyl, or $C_{6-14}$aryl.

In a further embodiment, $R_1$ and $R_2$ are independently or simultaneously $C_{1-10}$-(alkyl), $C_{2-10}$-(alkenyl), $C_{2-10}$-(alkynyl), $C_{3-10}$-(cycloalkyl) or $C_{6-10}$-(aryl), all of which are optionally substituted. In another embodiment, $R_1$ and $R_2$ are independently or simultaneously $C_{1-6}$-(alkyl), $C_{2-6}$-(alkenyl), $C_{2-6}$-(alkynyl), $C_{3-6}$-(cycloalkyl) or phenyl, all of which are optionally substituted. In another embodiment, $R_1$ and $R_2$ are independently or simultaneously methyl, ethyl, propyl, butyl or phenyl, all of which are optionally substituted. In a further embodiment, $R_1$ and $R_2$ are independently or simultaneously methyl, ethyl or propyl, all of which are optionally substituted. In a further embodiment, $R_1$ and $R_2$ are methyl.

In another embodiment of the disclosure, $R_3$ and $R_4$ are independently or simultaneously $C_{1-10}$-(alkyl), $C_{2-10}$-(alkenyl), $C_{2-10}$-(alkynyl), $C_{3-10}$-(cycloalkyl), $C_{6-10}$-(aryl), $C_{6-10}$-(heteroaryl)-O—$C_{1-10}$-(alkyl), —O—$C_{6-10}$-(aryl), —O—$CH_2$—$C_{6-10}$-(aryl), all of which are optionally substituted. In another embodiment, $R_3$ and $R_4$ are independently or simultaneously $C_{1-6}$-(alkyl), $C_{2-6}$-(alkenyl), $C_{2-6}$-(alkynyl), $C_{3-6}$-(cycloalkyl), phenyl, $C_{5-6}$-(heteroaryl)-O—$C_{1-6}$-(alkyl), —O-phenyl, —O—$CH_2$-phenyl, all of which are optionally substituted. In another embodiment, $R_3$ and $R_4$ are independently or simultaneously phenyl, tolyl (4-methylphenyl), anisyl (4-methoxyphenyl), xylyl (3,5-dimethylphenyl), 3,5-dimethyl-4-methoxy-phenyl, 3,5-di-tert-butyl-4-methoxy-phenyl or 3,5-bis(trifluoromethyl)-phenyl, all of which are optionally substituted.

In another embodiment, $R^3$ and $R^4$ are linked together to form an optionally substituted monocyclic or bicyclic, saturated, unsaturated and/or aromatic ring system having 4 to 14 atoms, including the phosphorous atom to which said groups are bonded, and in which one or more carbon atoms in said monocyclic or bicyclic ring system is optionally replaced with a heteromoiety selected from O, S, N, NH and $NC_{1-4}$ alkyl. In a further embodiment, $R^3$ and $R^4$ are linked together to form an optionally substituted monocyclic or bicyclic, saturated, unsaturated and/or aromatic ring system having 4 to 10 atoms, including the phosphorous atom to which said groups are bonded.

In another embodiment, the optional substituents are one or more of halo, OH, $NH_2$, $NHR^5$, $OR^5$, $NR^5R^6$ and $R^7$, in which $R^5$, $R^6$ and $R^7$ are simultaneously or independently selected from fluoro-substituted-$C_{1-4}$alkyl, $C_{1-4}$alkyl, $C_{2-4}$alkenyl, phenyl and $C_{1-4}$alkylenephenyl, specifically methyl, benzyl and phenyl.

(III) Processes of the Disclosure

The present disclosure also relates to a process for the production of compounds of the Formula (A), which are then utilized to produce compounds of the Formula (B). In particular, it has been determined that the reaction between a compound of the Formula (C) and an N-halosuccinimide results in high yields of the compounds of Formula (A), as shown in Scheme 1.

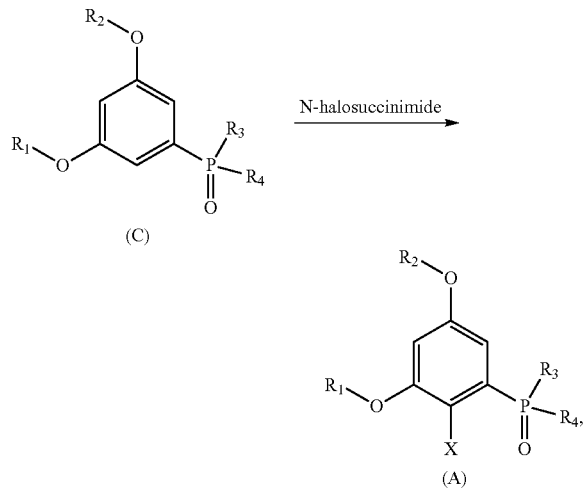

Scheme 1

(C)

(A)

wherein $R_1$-$R_4$ and X are as defined above.

Accordingly, the disclosure includes a process for producing a compound of the Formula (A) comprising:

(i) contacting a compound of the Formula (C)

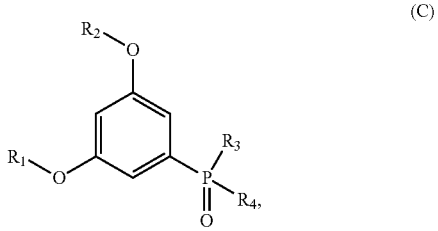

(C)

with an N-halosuccinimide to provide a compound of the Formula (A)

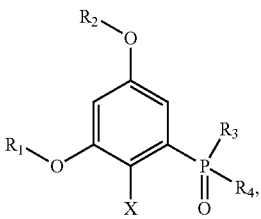

(A)

wherein $R_1$ and $R_2$ are independently or simultaneously $C_{1-20}$-(alkyl), $C_{2-20}$-(alkenyl), $C_{2-20}$-(alkynyl), $C_{3-20}$-(cycloalkyl) or $C_{6-14}$-(aryl), all of which are optionally substituted, $R_3$ and $R_4$ are independently or simultaneously $C_{1-20}$-(alkyl), $C_{2-20}$-(alkenyl), $C_{2-20}$-(alkynyl), $C_{3-20}$-(cycloalkyl), $C_{6-14}$-(aryl), $C_{6-14}$-(heteroaryl)-O—$C_{1-20}$-(alkyl), —O—$C_{6-14}$-(aryl), —O—$CH_2$—$C_{6-14}$-(aryl), all of which are optionally substituted, or $R^3$ and $R^4$ are linked together to form an optionally substituted monocyclic or polycylic ring system having 4 or more atoms, including the phosphorous atom to which said groups are bonded, and in which one or more carbon atoms in said monocyclic or polycyclic ring system is optionally replaced with a heteromoiety selected from O, S, N, $NR^5$, $SiR^5$ and $SiR^5R^6$, the optional substituents are selected from one or more of halo, $OR^5$, $NR^5R^6$ and $R^7$, $R^5$ and $R^6$ are simultaneously or independently H, fluoro-substituted-$C_{1-6}$alkyl, $C_{1-6}$alkyl, $C_{2-6}$alkenyl, $C_{2-6}$alkynyl or $C_{6-14}$aryl, $R^7$ is fluoro-substituted-$C_{1-6}$alkyl, $C_{1-6}$alkyl, $C_{2-6}$alkenyl, $C_{2-6}$alkynyl, or $C_{6-14}$aryl, and X is halo.

In a further embodiment, $R_1$ and $R_2$ are independently or simultaneously $C_{1-10}$-(alkyl), $C_{2-10}$-(alkenyl), $C_{2-10}$-(alkynyl), $C_{3-10}$-(cycloalkyl) or $C_{6-10}$-(aryl), all of which are optionally substituted. In another embodiment, $R_1$ and $R_2$ are independently or simultaneously $C_{1-6}$-(alkyl), $C_{2-6}$-(alkenyl), $C_{2-6}$-(alkynyl), $C_{3-6}$-(cycloalkyl) or phenyl, all of which are optionally substituted. In another embodiment, $R_1$ and $R_2$ are independently or simultaneously methyl, ethyl, propyl, butyl or phenyl, all of which are optionally substituted. In a further embodiment, $R_1$ and $R_2$ are independently or simultaneously methyl, ethyl or propyl, all of which are optionally substituted. In a further embodiment, $R_1$ and $R_2$ are methyl.

In another embodiment of the disclosure, $R_3$ and $R_4$ are independently or simultaneously $C_{1-10}$-(alkyl), $C_{2-10}$-(alkenyl), $C_{2-10}$-(alkynyl), $C_{3-10}$-(cycloalkyl), $C_{6-10}$-(aryl), $C_{5-10}$-(heteroaryl)-O—$C_{6-10}$-(aryl), —O—$CH_2$—$C_{6-10}$-(aryl), all of which are optionally substituted. In another embodiment, $R_3$ and $R_4$ are independently or simultaneously $C_{1-6}$-(alkyl), $C_{2-6}$-(alkenyl), $C_{2-6}$-(alkynyl), $C_{3-6}$-(cycloalkyl), phenyl, $C_{5-6}$-(heteroaryl)-O—$C_{1-6}$-(alkyl), —O-phenyl, —O—$CH_2$-phenyl, all of which are optionally substituted. In another embodiment, $R_3$ and $R_4$ are independently or simultaneously phenyl, tolyl (4-methylphenyl), anisyl (4-methoxyphenyl), xylyl (3,5-dimethylphenyl), 3,5-dimethyl-4-methoxy-phenyl, 3,5-di-tert-butyl-4-methoxy-phenyl or 3,5-bis(trifluoromethyl)-phenyl, all of which are optionally substituted.

In another embodiment, $R^3$ and $R^4$ are linked together to form an optionally substituted monocyclic or bicyclic, saturated, unsaturated and/or aromatic ring system having 4 to 14 atoms, including the phosphorous atom to which said groups are bonded, and in which one or more carbon atoms in said monocyclic or bicyclic ring system is optionally replaced with a heteromoiety selected from O, S, N, NH and $NC_{1-4}$ alkyl. In a further embodiment, $R^3$ and $R^4$ are linked together to form an optionally substituted monocyclic or bicyclic, saturated, unsaturated and/or aromatic ring system having 4 to 10 atoms, including the phosphorous atom to which said groups are bonded.

In another embodiment, the optional substituents are one or more of halo, OH, $NH_2$, $NHR^5$, $OR^5$, $NR^5R^6$ and $R^7$, in which $R^5$, $R^6$ and $R^7$ are simultaneously or independently selected from fluoro-substituted-$C_{1-4}$alkyl, $C_{1-4}$alkyl, $C_{2-4}$alkenyl, phenyl and $C_{1-4}$alkylenephenyl, specifically methyl, benzyl and phenyl.

In another embodiment, X is F, Cl, Br or I. In another embodiment, X is Cl or Br.

In another embodiment, the N-halosuccinimide is N-fluorosuccinimide, N-clorosuccinimide, N-bromosuccinimide or N-iodosuccinimide.

In another embodiment, the process is performed at a temperature between −20° C. and 20° C.

The present disclosure also provides a process for the Ullman coupling of compounds of the Formula (A) to provide the biaryl disphosphine ligands of the Formula (B). Accordingly, in an embodiment of the present disclosure, there is a process for the production of biaryl disphosphine ligands of the Formula (B), comprising, (i) contacting a compound of the Formula (A),

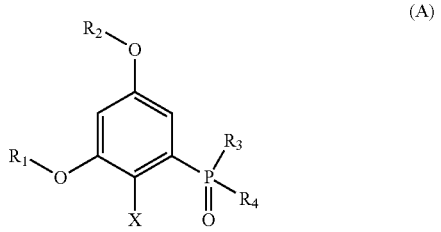

with copper powder and isolating a compound of the Formula (E),

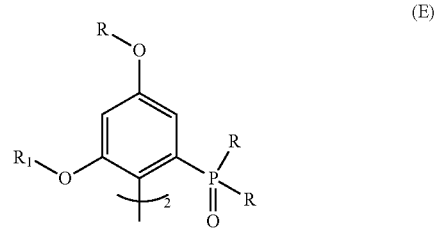

wherein $R_1$ and $R_2$ are independently or simultaneously $C_{1-20}$-(alkyl), $C_{2-20}$-(alkenyl), $C_{2-20}$-(alkynyl), $C_{3-20}$-(cycloalkyl) or $C_{6-14}$-(aryl), all of which are optionally substituted, $R_3$ and $R_4$ are independently or simultaneously $C_{1-20}$-(alkyl), $C_{2-20}$-(alkenyl), $C_{2-20}$"-(alkynyl), $C_{3-20}$-(cycloalkyl), $C_{6-14}$-(aryl), $C_{5-14}$-(heteroaryl)-O—$C_{1-20}$-(alkyl), —O—$C_{6-14}$-(aryl), —O—$CH_2$—$C_{6-14}$-(aryl), all of which are optionally substituted, or $R^3$ and $R^4$ are linked together to form an optionally substituted monocyclic or polycylic ring system having 4 or more atoms, including the phosphorous atom to which said groups are bonded, and in which one or more carbon atoms in said monocyclic or polycyclic ring system is optionally replaced with a heteromoiety selected from O, S, N, $NR^5$, $SiR^5$ and $SiR^5R^6$, the optional substituents are selected from one or more of halo, $OR^5$, $NR^5R^6$ and $R^7$, $R^5$ and $R^6$ are simultaneously or independently H, fluoro-substituted-$C_{1-6}$alkyl, $C_{1-6}$alkyl, $C_{2-6}$alkenyl, $C_{2-6}$alkynyl or $C_{6-14}$aryl, $R^7$ is fluoro-substituted-$C_{1-6}$alkyl, $C_{1-6}$alkyl, $C_{2-6}$alkenyl, $C_{2-6}$alkynyl, or $C_{6-14}$aryl, and X is halo.

In another embodiment, the Ullman coupling reaction is performed by heating a compound of the Formula (A) in an inert organic solvent, such as DMF with the copper powder, activated with iodine, for example, to a temperature of about 100° C. to about 200° C.

In another embodiment of the disclosure, the compound of the Formula (E) is further subjected to a reduction reaction to produce the biaryl diphosphine ligands of the Formula (B), incorporating all of the definitions as described above. In an embodiment, the reduction reaction comprises contacting the compound of the Formula (E) with tri-chloro silane to reduce the phosphonate moieties to a phosphine moieties.

In another embodiment, compounds of the Formula (B) are separated into their individual (R) and (S) isomers.

In another embodiment of the disclosure, the compounds of the Formula (B) are produced from easily accessible starting materials such as 3,5-dimethoxy-bromobenzene. For example, Scheme 1, illustrates the synthesis of a compound of the Formula (B) from 3,5-dimethoxy-bromobenzene.

Scheme 1

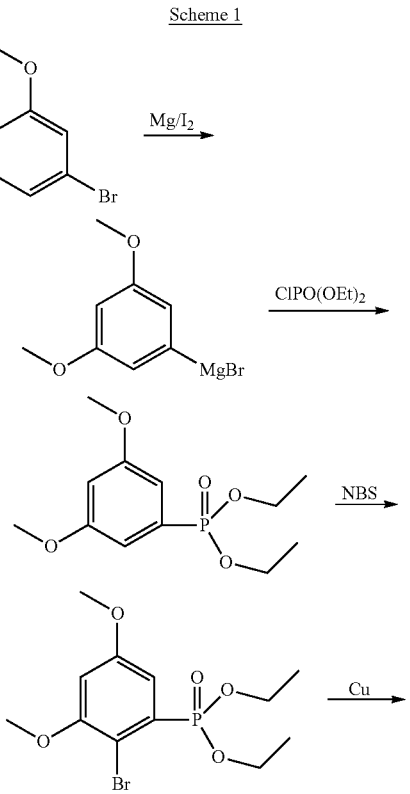

-continued
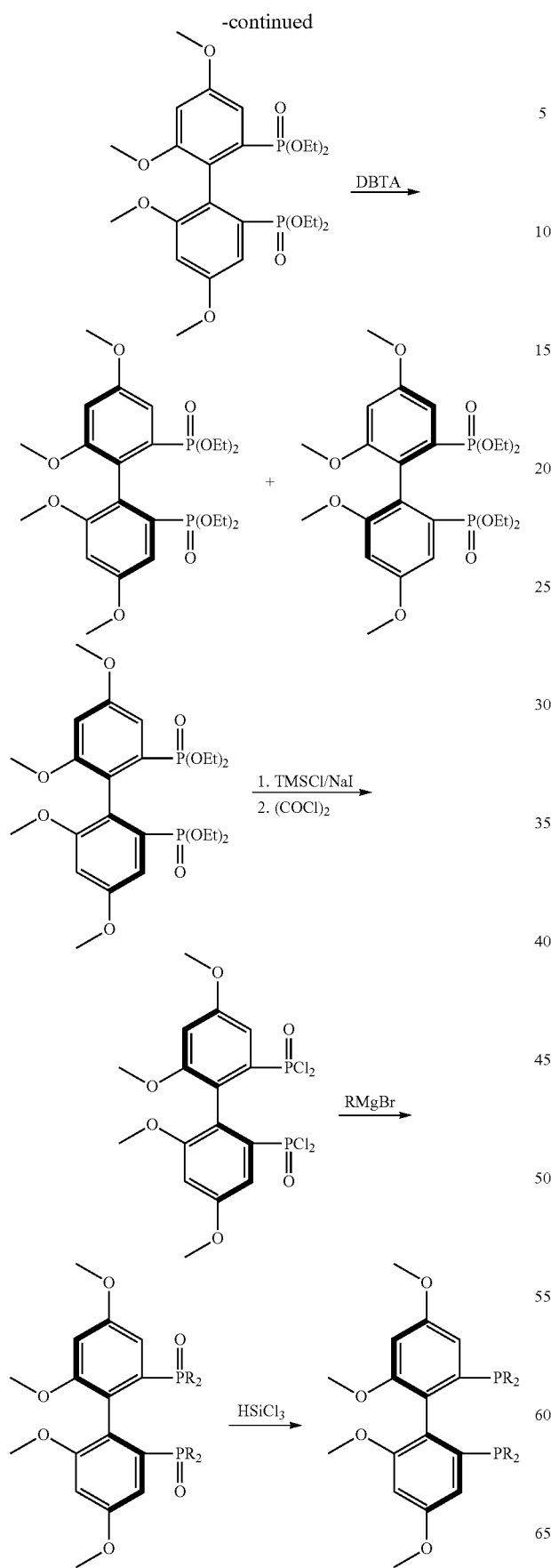
In another embodiment, as shown in Scheme 2, is illustrated another generic synthesis for a compound of the Formula (B).
Scheme 2
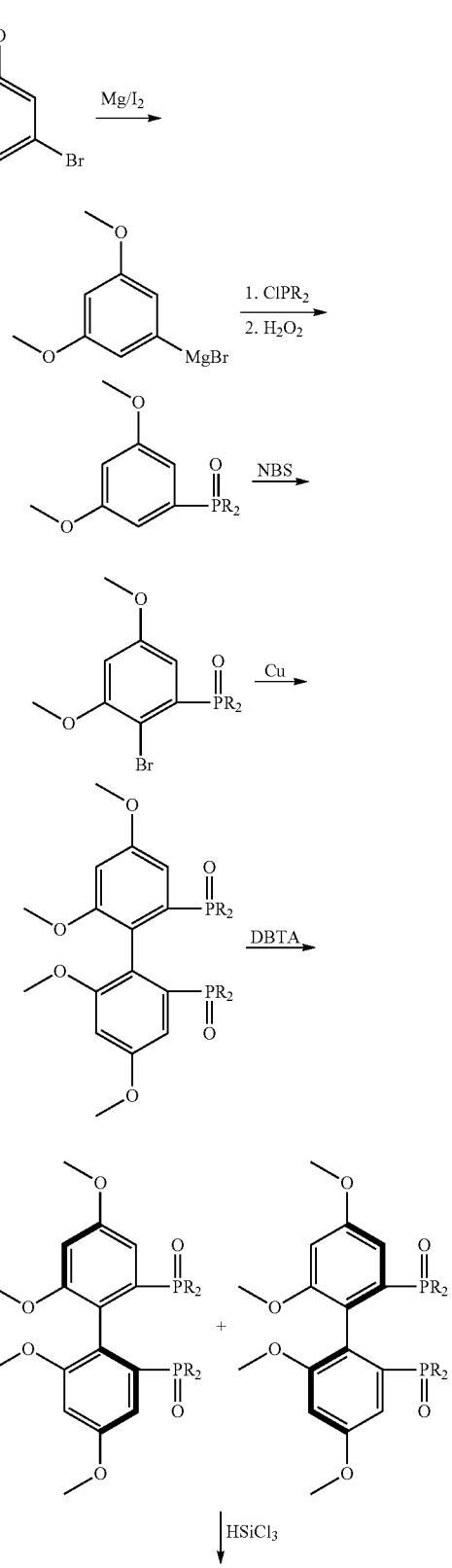

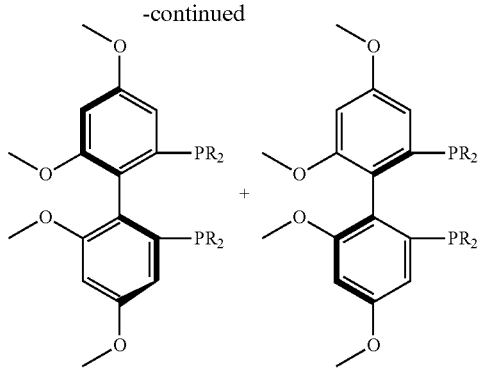

(IV) Metal Complexes of Compounds of the Formula (B)

The present disclosure also provides metal complexes, such as transition metal complexes, incorporating the biaryl diphosphine ligands of the Formula (B). The metal complexes incorporating the compounds of the Formula (B) are useful in a variety of catalytic processes including asymmetric hydrogenation of a variety of prochiral substrates.

In an embodiment, the catalytic reactions include, but are not limited to hydrogenation, transfer hydrogenation, hydroformylation, hydrosilylation, hydroboration, hydroamination, hydrovinylation, hydroarylation, hydration, isomerizations oxidation, epoxidation, C—C bond formation, C—X bond formation, functional group interconversion, kinetic resolution, dynamic kinetic resolution, cycloaddition, Diels-Alder reaction, retro-Diels-Alder reaction, sigmatropic rearrangement, electrocyclic reaction, olefin metathesis, polymerization, carbonylation and aziridination. In an embodiment, the metal complexes of the present disclosure are used as catalysts for asymmetric hydrogenation. In a further embodiment, the asymmetric hydrogenation comprises the hydrogenation of a substrate possessing at least one C=C, C=N and/or C=O bond. In another embodiment, the substrate containing the at least one C=C, C=N and/or C=O bond is prochiral, and the hydrogenated product is chiral and enantiomerically enriched with an enantiomeric excess of at least 50%, optionally 80% or 90%.

In an embodiment, the metal complexes incorporating the compounds of the Formula (B) are isolated or alternatively, are generated in situ.

In another embodiment, the transition metal complexes containing compounds of Formula (B) include any metal that has catalytic activity such as iron, ruthenium, osmium, cobalt, rhodium, iridium, nickel, palladium, platinum, copper, silver, gold, etc. In another embodiment, the metal is ruthenium or rhodium.

In another embodiment, the metal complex of the present disclosure is a compound of the formula [RuX$_2$(ligand)(B)], wherein X is halo and ligand is any neutral ligand such as p-cymene, COD. In another embodiment, the metal complex is RuCl$_2$(p-cycmene)((R)-Ph-Garphos) or RuCl$_2$(p-cycmene)((R)-DMM-Garphos).

In another embodiment, the metal complex of the present disclosure is a compound of the formula [RuX$_2$(diamine)(B)], wherein X is halo and diamine is any diamino ligand, such as DPEN, DAIPEN. In another embodiment, the metal complex is RuCl$_2$((S)-Ph-Garphos)(S,S-DPEN), RuCl$_2$((S)-Ph-Garphos)(S)-DAIPEN), RuCl$_2$((S)-Xylyl-Garphos)(S,S-DPEN), RuCl$_2$((S)-Xylyl-Garphos)(S)-DAIPEN), RuClA(S)-DMM-Garphos)(S,S-DPEN) or RuCl$_2$((S)-DMM-Garphos)((S)-DAIPEN).

In another embodiment, the metal complex of the present disclosure is a compound of the formula [Rh(ligand)(B)][X], wherein ligand is any neutral ligand such as p-cymene, COD and X is any anionic ligand, such as BF$_4$. In another embodiment, the metal complex is [Rh(COD)((R)-Ph-Garphos)][BF$_4$], [Rh(COD)((R)-Xylyl-Garphos)][BF$_4$] or [Rh(COD)((R)-DMM-Garphos)][BF$_4$]. In the above embodiments, Garphos represents

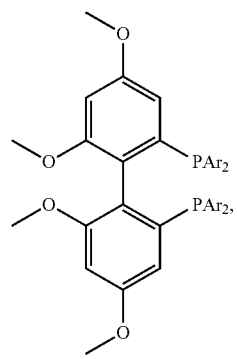

in which Ar represents phenyl (Ph), xylyl or 3,5-dimethyl-4-methoxyphenyl (DMM).

In another embodiment, there is also included a metal complex containing a compound of formula (B). In another embodiment, the metal has catalytic activity, such as iron, ruthenium, osmium, cobalt, rhodium, iridium, nickel, palladium, platinum, copper, silver or gold. In another embodiment of the disclosure, there is included a use of a metal complex containing a compound of formula (B) for catalysis, such as hydrogenation In another embodiment of the disclosure, when the catalytic reaction is a hydrogenation, the hydrogenation conditions optionally comprise a base. For example, bases include organic non-coordinating bases such as DBU, an alkaline or alkaline-earth metal carbonate, a carboxylate salt such as sodium or potassium acetate, or an alcoholate or hydroxide salt. In an embodiment of the disclosure, the bases are the alcoholate or hydroxide salts selected from the group consisting of the compounds of formula (R'O)$_2$M' and R'OM", wherein M' is an alkaline-earth metal, M" is an alkaline metal and a stands for hydrogen or a linear or branched C$_{1-20}$alkyl group.

Standard hydrogenation conditions, as used herein, typically implies the mixture of the substrate with a metal complex of Formula (I), (II), (III), (IV) or (V) with or without a base, possibly in the presence of a solvent, and then treating such a mixture with a hydrogen donor solvent at a chosen pressure and temperature (transfer hydrogenation) or in an atmosphere of hydrogen gas at a chosen pressure and temperature. Varying the reaction conditions, including for example, temperature, pressure, solvent and reagent ratios, to optimize the yield of the desired product would be well within the abilities of a person skilled in the art.

The present application also provides processes for the preparation of chiral compounds which are precursors for certain chiral pharmaceuticals. Such precursors include, but are not limited to compounds for the preparation of Atorvastatin, Rosuvastatin, Aprepitant, Montelukast and Duloxetine. For example, in one process, the chiral alcohol (S)-ethyl 4-chloro-3-hydroxybutanoate is prepared by the catalytic hydrogenation of the ketone ethyl 4-chloro-3-oxobutanoate, as shown in Scheme 3.

Scheme 3

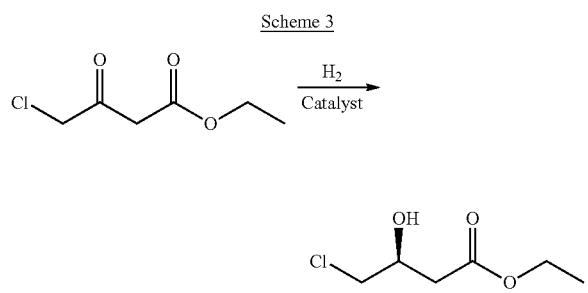

(S)-ethyl 4-chloro-3-hydroxybutanoate is a precursor for the synthesis of Atorvastatin, Rosuvastatin and other statins, and in an embodiment, is synthesized from the ketone ethyl 4-chloro-3-oxobutanoate using metal complexes incorporating the compounds of the formula (B) in a hydrogenation reaction.

In another embodiment, the chiral alcohol (R)-1-(3,5-bis(trifluoromethyl)-phenyl)ethanol is prepared by the catalytic hydrogenation of the ketone 1-(3,5-bis(trifluoromethyl)phenyl)ethanone, as shown in Scheme 4.

Scheme 4

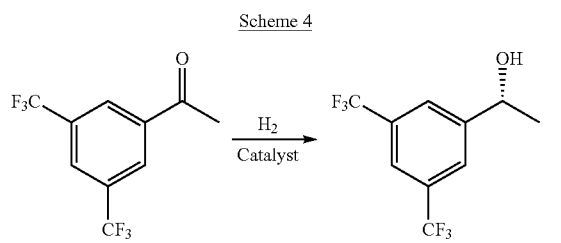

(R)-1-(3,5-bis(trifluoromethyl)-phenyl)ethanol is a precursor for the synthesis of Aprepitant, and in an embodiment, is synthesized from the ketone 1-(3,5-bis(trifluoromethyl)phenyl)ethanone using metal complexes incorporating the compounds of the formula (B) in a hydrogenation reaction.

In another embodiment, the chiral alcohol (R,E)-methyl 2-(3-(3-(2-(7-chloroquinolin-2-yl)vinyl)phenyl)-3-hydroxypropyl)benzoate is prepared by the catalytic hydrogenation of the corresponding ketone, as shown in Scheme 5.

Scheme 5

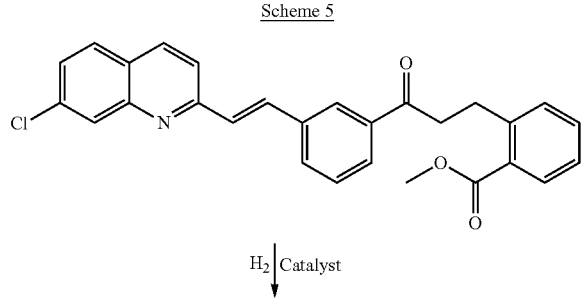

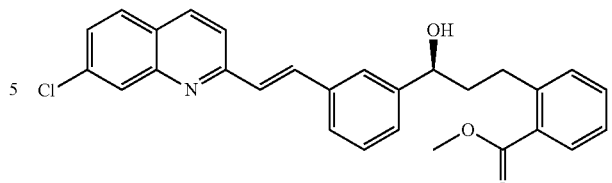

(R,E)-Methyl-2-(3-(3-(2-(7-chloroquinolin-2-yl)vinyl)phenyl)-3-hydroxypropyl)-benzoate is a precursor for the synthesis of Montelukast, and in an embodiment, is synthesized from the corresponding ketone using metal complexes incorporating the compounds of the formula (B) in a hydrogenation reaction.

In another embodiment, the chiral alcohol S)-3-(methylamino)-1-(thiophen-2-yl)propan-1-ol is prepared by the catalytic hydrogenation of the corresponding ketone, as shown in Scheme 6.

Scheme 6

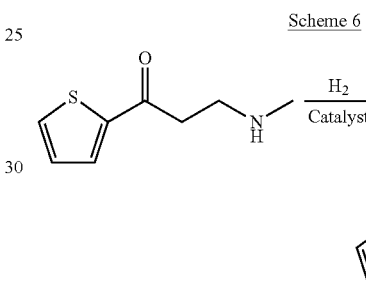

(S)-3-(Methylamino)-1-(thiophen-2-yl)propan-1-ol is a precursor for the synthesis of Duloxetine, and in an embodiment, is synthesized from the corresponding ketone using metal complexes incorporating the compounds of the formula (B) in a hydrogenation reaction.

The following non-limiting examples are illustrative of the present disclosure:

EXAMPLES

The disclosure will now be described in further details by way of the following examples, wherein the temperatures are indicated in degrees centigrade and the abbreviations have the usual meaning in the art. All the procedures described hereafter have been carried out under an inert atmosphere unless stated otherwise. All preparations and manipulations were carried out under $H_2$, $N_2$ or Ar atmospheres with the use of standard Schlenk, vacuum line and glove box techniques in dry, oxygen-free solvents. Tetrahydrofuran (THF), diethyl ether ($Et_2O$) and hexanes were dried and distilled from sodium benzophenone ketyl. Deuterated solvents were degassed and dried over activated molecular sieves. NMR spectra were recorded on a 300 MHz spectrometer (300 MHz for $^1H$, 75 MHz for $^{13}C$ and 121.5 for $^{31}P$). All $^{31}P$ chemical shifts were measured relative to 85% $H_3PO_4$ as an external reference. $^1H$ and $^{13}C$ chemical shifts were measured relative to partially deuterated solvent peaks but are reported relative to tetramethylsilane.

Example 1(a)

Preparation of diethyl 3,5-dimethoxyphenylphosphonate

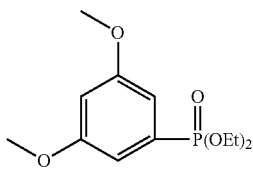

A solution of 1-bromo-3,5-dimethoxybenzene (20 g, 92.1 mmol) in THF (100 ml) was added to a flask (500 ml) with magnesium (2.5 g, 103 mmol), $I_2$ (20 mg) and THF (50 ml) and refluxed for 2 h. The resulting light brown solution was transferred to another flask (500 ml) and was cooled to −78° C. Diethyl phosphorochloridate (17.8 g, 103 mmol) in THF (80 ml) was added at −78° C. within 1 h. The mixture was stirred at −78° C. for 1 h, then slowly warmed up to RT and stirred at RT overnight. Brine (20%, 200 ml) was added to the mixture and it was stirred for 30 min. The organic layer was separated and the aqueous layer was extracted with ethyl acetate (200 ml×1) and $CH_2Cl_2$ (100 ml×1). The combined organic layer was washed with brine (300 ml×2) and dried over $MgSO_4$. It was filtered and the solvent was removed. The residues were purified with silica gel pad (eluent: $CH_2Cl_2$ to removed impurities, then $CH_2Cl_2$/THF=10/1 to wash out the product). The pure product was obtained as pale a yellow oil after the solvent was removed (20.2 g, 80% yield). $^1$H NMR (300 Mhz, $CD_2Cl_2$) δ: 6.90 (dd, $J_1$=2.1 Hz, $J_2$=14.7 Hz, 2H), 6.63 (d, J=2.1 Hz, 1H), 4.05 (quart, J=6.9 Hz, 4H), 3.83 (s, 6H), 1.31 (t, J=6.9 Hz, 6H). $^{31}$P NMR (121.5 MHz, $CD_2Cl_2$) δ: 19.10.

Example 2

Preparation of diethyl 2-bromo-3,5-dimethoxyphenylphosphonate

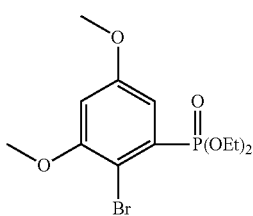

N-Bromosuccinimide (NBS) (8.9 g, 50 mmol) was added to the solution of diethyl 3,5-dimethoxyphenylphosphonate (12.5 g, 45.6 mmol) in $CH_2Cl_2$ (150 ml) at 0° C. The resulting suspension was stirred at 0° C. for 6 h. $Na_2CO_3$ (saturated, 60 ml) was added to quench the reactions. It was stirred at RT for 30 min, the organic layer was separated and the aqueous layer was extracted with $CH_2Cl_2$ (80 ml×1). The combined organic layer was washed with brine and dried over $MgSO_4$. It was filtered and the solvent was removed to give the crude product as a pale yellow oil (14 g, 87% yield). It was sufficiently pure enough for the next step. The pure sample was obtained by chromatography. $^1$H NMR (300 MHz, $CD_2Cl_2$) δ: 7.16 (dd, $J_1$=3.0 Hz, $J_2$=15.3 Hz, 1H), 6.67 (d, J=3.0 Hz, 1H), 4.20-4.06 (m, 4H), 3.89 (s, 3H), 3.85 (s, 3H), 1.34 (t, J=7.2 Hz, 6H). $^{31}$P NMR (121.5 MHz, $CD_2Cl_2$) δ: 15.59. $^{13}$C NMR (75.5 MHz, $CD_2Cl_2$) δ: 159.77 (d, $J_{c-p}$=20.0 Hz), 157.66 (d, $J_{c-p}$=19.0 Hz), 131.49 (d, Jc-p=189.2 Hz), 112.04 (d, Jc-p=8.7 Hz), 105.52 (d, Jc-p=4.5 Hz), 103.51 (d, Jc-p=2.9 Hz), 62.73, 62.66, 56.78, 55.96, 16.34, 16.26.

Example 3

Preparation of (R,S)-tetraethyl 4,4',6,6'-tetramethoxybiphenyl-2,2'-diyldiphosphonate

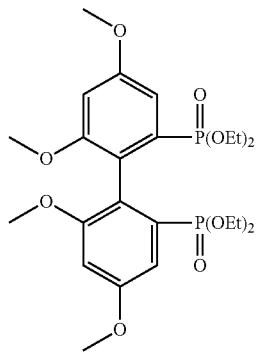

Copper powder (4.23 g, 68 mmol) was added to a solution of diethyl 2-bromo-3,5-dimethoxyphenylphosphonate (8.0 g, 22.7 mmol) in DMF (30 ml). The suspension was stirred at 140° C. for 2 h. DMF was removed under vacuum. The residues were stirred with $CHCl_3$ (80 ml) for 30 min. It was filtered and the solid was washed with $CHCl_3$ (50 ml). The combined organic layer was washed with diluted $NH_4OH$ (5%) in brine (100 ml), then brine (100 ml) and dried over $MgSO_4$. It was filtered through a silica gel pad (eluent: $CHCl_3$/THF=15/1 to removed impurities, then $CH_2Cl_2$/THF=1/1 to washed out the product). The solvent was removed from the filtrate to give the product as a pale-yellow solid which was recrystallized from $CH_2Cl_2$/Ether (1/10) to give the pure product as a colorless crystalline solid (3.1 g, 50% yield). $^1$H NMR (300 MHz, $CD_2Cl_2$) δ: 7.02 (ddd, $J_1$=0.9 Hz, $J_2$=2.4 Hz, $J_3$=15.0 Hz, 2H), 6.66 (d, J=2.4 Hz, 2H), 4.02-3.78 (m, 8H), 3.88 (s, 6H), 3.68 (s, 6H), 1.20 (t, J=7.0 Hz, 6H), 1.14 (t, J=7.0 Hz, 6H). $^{31}$P NMR (121.5 MHz, $CD_2Cl_2$) δ: 18.27.

Example 4

Resolution of (R,S)-tetraethyl 4,4',6,6'-tetramethoxybiphenyl-2,2'-diyldiphosphonate

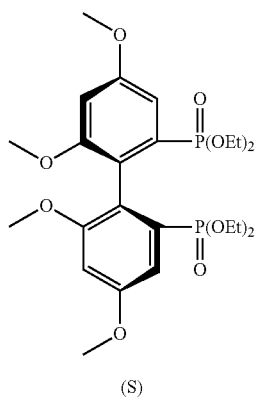

(S)

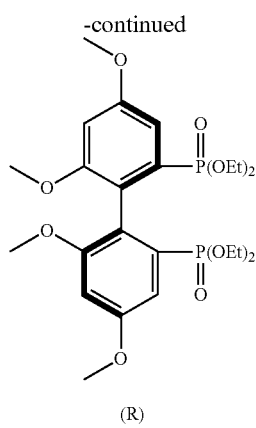

(R)

Tetraethyl-4,4',6,6'-tetramethoxybiphenyl-2,2'-diyl-diphosphonate (1.82 g, 3.3 mmol) was dissolved in CH$_2$Cl$_2$ (4.5 ml). L-(−)-DBTA monohydrate (1.35 g, 3.6 mmol) in ether (20 ml) was added. Another portion of ether (30 ml) was added slowly. The suspension was stirred at RT for 1 h. It was filtered to give a white solid (1.32 g, 82% ee) which was re-dissolved in CH$_2$Cl$_2$ (3.2 ml), ether (50 ml) was added. The resulting suspension was stirred for 1 h. The solid was collected by filtration (0.97 g, 97.5% ee) which was recrystallized one more time to give the (S)-form/(−)-DBTA complex (0.8 g, 99% ee). The complex was dissolved in CH$_2$Cl$_2$ (30 ml) and was washed with NaHCO$_3$ (saturated, 40 ml×2), brine (40 ml). The organic layer was dried over MgSO$_4$ for 2 h. It was filtered and the solvent was removed from the filtrate to give the (S)-form enantiomer as a colorless solid (0.46 g, 50% yield, >99% ee). $[\alpha]^{25}_D = -22.8°$ (C=1.1, CHCl$_3$). The combined mother liquor was free with NaHCO$_3$ and was resolved with D-(+)-DBTA to give the (R)-form enantiomer as a colorless solid (0.53 g, 58% yield, >99% ee). $[\alpha]^{25}_D = +23.0°$ (C=1.0, CHCl$_3$). (HPLC: Chiralpak AS-H column 0.46 cm×25 cm. 2-PrOH/Hexane=15/85, 1 ml/min, 25° C., 254 nm. (S)-form=6.96 min, (R)-form=4.9 min).

Example 5

Preparation of (R)-4,4',6,6'-tetramethoxybiphenyl-2,2'-diyldiphosphonic dichloride

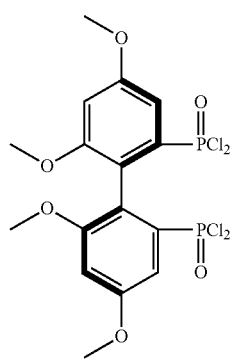

Thionyl chloride (0.4 ml, 650 mg, 5.5 mmol) was added to the mixture of (R)-tetraethyl-4,4',6,6'-tetramethoxybiphenyl-2,2'-diyldiphosphonate (220 mg, 0.4 mmol) and DMF (0.08 ml). The resulting mixture was stirred at 80-90° C. for 3 h. All volatiles were removed under vacuum. The residues were recrystallized from CH$_2$Cl$_2$/Hexane to give white solid. $^{31}$P NMR (121.1 MHz, CD$_2$Cl$_2$) δ: 34.45.

Example 6

Preparation of (R)-4,4',6,6'-tetramethoxybiphenyl-2,2'-diyl-bis(diphenylphosphine oxide)

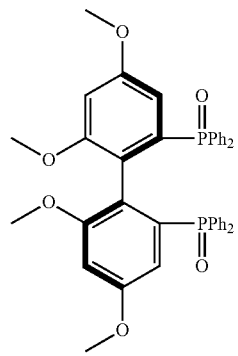

Phenylmagnesium bromide (1.0 M in THF, 6 mmol) was added to the solution of 4,4',6,6'-tetramethoxybiphenyl-2,2'-diyldiphosphonic dichloride (0.5 mmol) in THF (3 ml) at −78° C. The mixture was stirred at −78° C. for 1 h, then it was slowly warmed up to RT and stirred at RT for another 1 h. NH$_4$Cl (saturated, 30 ml) was added. The organic layer was separated and the aqueous layer was extracted with CH$_2$Cl$_2$ (40 ml×2). The combined organic layer was washed with brine and dried over MgSO$_4$. The solvent was removed and the residues were purified with silica gel chromatography (eluent: CH$_2$Cl$_2$/THF=10/1, then CH$_2$Cl$_2$/THF=1/1 to washed out the product). The solvent was removed to give the product as a white solid. $^1$H NMR (300 MHz, CD$_2$Cl$_2$) δ: 7.75-7.62 (m, 8H), 7.55-7.40 (m, 8H), 7.38-7.35 (m, 4H), 6.39 (d, J=2.1 Hz, 2H), 6.32 (dd, J$_1$=2.1 Hz, J$_2$=14.4 Hz, 2H), 3.67 (s, 6H), 3.06 (s, 6H). $^{31}$P NMR (121.1 MHz, CD$_2$Cl$_2$) δ: 30.17.

Example 7

Preparation of (R)-4,4',6,6'-tetramethoxybiphenyl-2,2'-diyl-bis(diphenylphosphine)

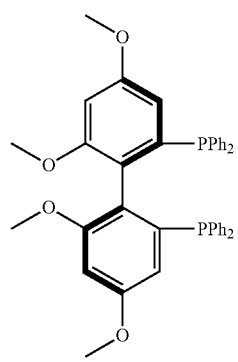

HSiCl$_3$ (0.2 ml. 268 mg, 1.98 mmol) was added to the suspension of (R)-4,4',6,6'-tetramethoxy-biphenyl-2,2'-diyl-bis(diphenylphosphineoxide) (50 mg, 0.074 mmol) in toluene (6 ml). The resulting mixture was reflux for 20 h under Ar. It was cooled to RT and NaOH (2N, 30 ml) was added and the resulting mixture was stirred at 50° C. for 30 min. The organic layer was separated and the aqueous layer was extracted with ethyl acetate (30 ml×1). The combined organic layer was washed with brine and dried over MgSO$_4$. It was filtered though a silica gel pad. The solvent was removed to give the product as a white solid (40 mg, 84%). $^1$H NMR (300 MHz, CD$_2$Cl$_2$) δ: 7.35-7.24 (m, 16H), 7.18-7.11 (m, 4H), 6.33 (d, J=2.1 Hz, 2H), 6.24-6.21 (m, 2H), 3.62 (s, 6H), 3.15 (s, 6H). $^{31}$P NMR (121.1 MHz, CD$_2$Cl$_2$) δ: −12.32.

Example 8

Preparation of (S)-4,4',6,6'-tetramethoxybiphenyl-2,2'-diyl-bis(diphenylphosphine)

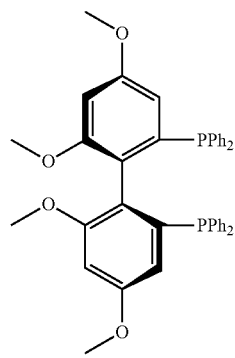

(S)-4,4',6,6'-tetramethoxy-biphenyl-2,2'-diyl-bis(diphenylphosphine) was prepared from (S)-4,4',6,6'-tetramethoxybiphenyl-2,2'-diyl-bis(diphenylphosphineoxide) using the procedure outlined in Example 7.

Example 9

Preparation of (R)-(4,4',6,6'-tetramethoxybiphenyl-2,2'-diyl)bis(bis(4-methoxyphenyl)phosphine oxide

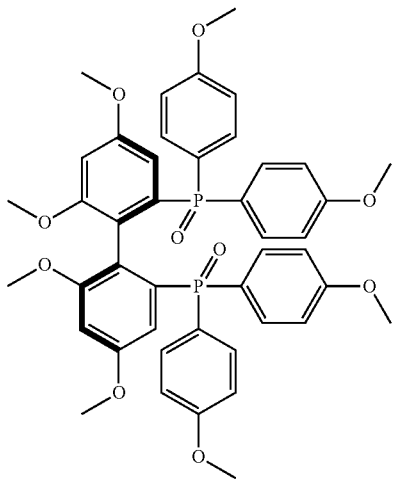

Me$_3$SiCl (0.81 g, 7.4 mmol) was added to the solution of NaI (1.1 g, 7.4 mmol) and (R)-tetraethyl-4,4',6,6'-tetramethoxybiphenyl-2,2'-diyldiphosphonate (1.0 g, 1.83 mmol) in CH$_3$CN (12 ml). The resulting suspension was stirred at 50° C. for 2 h. All volatiles were removed under vacuum. Dried CH$_2$Cl$_2$ (12 ml) was added to the residues, along with a few drops of DMF and then oxalyl chloride (3 g, 23.8 mmol). The resulting mixture was stirred at 40° C. for 4 h. It was filtered and all volatiles were removed from the filtrate to give the tetrachloride intermediate which was dissolved in THF (30 ml). It was cooled with a dry-ice bath and (4-methoxyphenyl)magnesium bromide (0.5M in THF, 30 ml, 15 mmol) was added at −78° C. The resulting mixture was stirred at −78° C. for 0.5 h, then was slowly warmed up to RT and stirred for 1 h. NH$_4$Cl (saturated, 30 ml) and water (20 ml) was added to quench the reactions. The organic layer was separated and the aqueous layer was extracted with ethyl acetate (40 ml×1). The combined organic layer was washed with brine (saturated, 80 ml×2) and dried over MgSO$_4$. It was filtered and the solvent was removed from the filtrate to give the crude product as a pale yellow solid which was purified with silica gel chromatography (eluent: CH$_2$Cl$_2$/THF=10/3 to 10/4). The solvent was removed to give the product as a pale yellow solid (1.1 g, 76% yield). $^1$H NMR (CD$_2$Cl$_2$): δ 7.46-7.40 (m, 8H), 6.84-6.75 (m, 8H), 6.23-6.18 (m, 4H), 3.73 (s, 6H), 3.70 (s, 6H), 3.55 (s, 6H), 3.05 (s, 6H). $^{13}$P NMR: δ 30.75.

Example 10

Preparation of (R)-(4,4',6,6'-tetramethoxybiphenyl-2,2'-diyl)bis(bis(4-methoxyphenyl)phosphine)

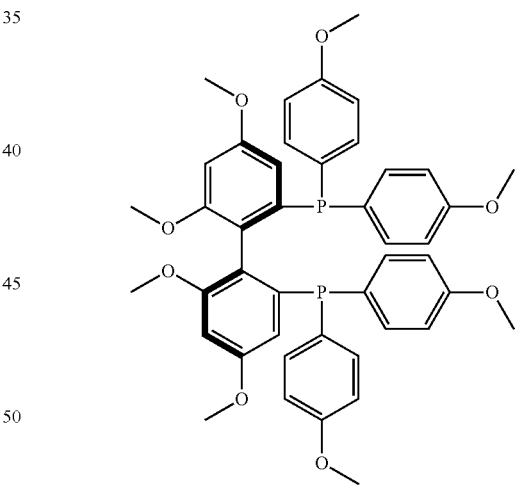

HSiCl$_3$ (2.1 ml) was added to the reaction mixture of (R)-(4,4',6,6'-tetramethoxybiphenyl-2,2'-diyl)bis(bis(4-methoxyphenyl)phosphine oxide) (0.57 g, 0.72 mmol) and toluene (50 ml). The cloudy mixture was heated at 110° C. overnight. It was cooled to RT, NaOH (80 ml, 2M) was added slowly and stirred for 30 min. The organic layer was separated and the aqueous layer was extracted with toluene (40 ml). The combined organic layer was washed with brine (30 ml), passed through a shout silica gel pad (CH$_2$Cl$_2$/THF=6/1 as eluent). All solvents were removed from filtrate and dried under vacuum to give the product as a white solid (0.43 g, 78%). $^1$H NMR (300 MHz, CD$_2$Cl$_2$): δ 7.08-7.03 (m, 4H), 7.00-6.94 (m, 4H), 6.76-6.69 (m, 8H), 6.20 (d, J=2.1 Hz, 2H), 6.13-6.11

(m, 2H), 3.69 (s, 6H), 3.68 (s, 6H), 3.55 (s, 6H), 3.07 (s, 6H). $^{31}$P NMR (121.5 MHz, CD$_2$Cl$_2$) δ: −15.2 ppm (s).

Example 11

Preparation of (S)-(4,4',6,6'-tetramethoxybiphenyl-2,2'diyl)bis(bis(4-methoxyphenyl)phosphine)

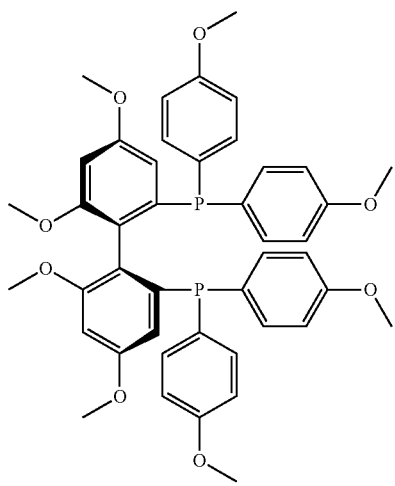

(S)-(4,4',6,6'-tetramethoxybiphenyl-2,2'-diyl)bis(bis(4-methoxphenyl)phosphine) was prepared from (S)-(4,4',6,6'-tetramethoxybiphenyl-2,2'-diyl)bis(bis(4-methoxyphenyl)phosphine oxide) using the procedure outlined in Example 10.

Example 12

Preparation of (R)-(4,4',6,6'-tetramethoxybiphenyl-2,2'-diyl)bis(bis(4-methylphenyl)phosphine oxide)

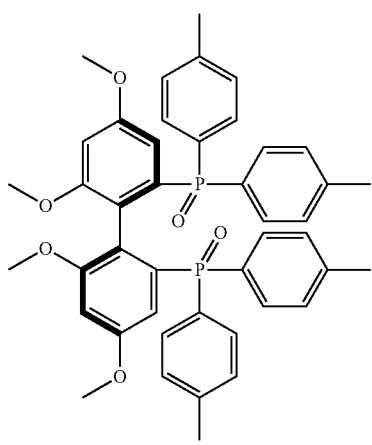

Me$_3$SiCl (0.86 g, 7.5 mmol) was added to the solution of NaI (1.12 g, 7.5 mmol) and (R)-tetraethyl-4,4',6,6'-tetramethoxybiphenyl-2,2'-diyldiphosphonate (1.04 g, 1.90 mmol) in CH$_3$CN (10 ml). The resulting suspension was stirred at 50° C. for 2 h. All volatiles were removed under vacuum. Dried CH$_2$Cl$_2$ (12 ml) was added to the residues, along with a few drops of DMF and then oxalyl chloride (3 g, 23.8 mmol). The resulting mixture was stirred at 40° C. for 4 h. It was filtered and all volatiles were removed from the filtrate to give the tetrachloride intermediate which was dissolved in THF (30 ml). It was cooled with a dry-ice bath, and (4-methylphenyl)magnesium bromide (0.5M in THF, 30 ml, 15 mmol) was added at −78° C. The resulting mixture was stirred at −78° C. for 0.5 h, then was slowly warmed up to RT and stirred for 1 h. NH$_4$Cl (saturated, 30 ml) and water (20 ml) was added to quench the reactions. The organic layer was separated and the aqueous layer was extracted with ethyl acetate (40 ml×1). The combined organic layer was washed with brine (saturated, 80 ml×2) and dried over MgSO$_4$. It was filtered and the solvent was removed from the filtrate to give the crude product as a pale yellow solid which was purified with silica gel chromatography (eluent: CH$_2$Cl$_2$/THF=10/3 to 10/4). The solvent was removed to give the product as a pale yellow solid (1.32 g, 95% yield). $^1$H NMR (CD$_2$Cl$_2$): δ 7.56-7.42 (m, 8H), 7.25 (m, 4H), 7.15-7.13 (m, 4H), 6.32-6.27 (m, 4H), 3.65 (s, 6H), 3.10 (s, 6H), 2.40 (s, 6H), 2.35 (s, 6H). $^{13}$P NMR: δ 30.0.

Example 13

Preparation of (R)-(4,4',6,6'-tetramethoxybiphenyl-2,2'diyl)bis(bis(4-methylphenyl)phosphine)

A sample of (R)-(4,4',6,6'-tetramethoxybiphenyl-2,2'-diyl)bis(bis(4-methylphenyl)phosphine oxide) (0.58 g, 0.79 mmol) was dissolved in toluene (40 ml) and HSiCl$_3$ (2.8 ml) was added to the reaction mixture. The cloudy mixture was heated at 110° C. with stirring until it became clear (around 20 hours), cooled to RT and NaOH (80 ml, 2M) was added slowly and the mixture stirred for 30 min. The organic layer was separated and the aqueous layer was extracted with toluene (40 ml). The combined organic layer was washed with brine (30 ml), passed through a short silica gel pad (CH$_2$Cl$_2$ as eluent) and the solvent was removed from the filtrate and dried under vacuum to give the product as a white solid (0.43 g, 80%). $^1$H NMR (CD$_2$Cl$_2$): δ 7.02-7.01 (m, 8H), 6.95-6.97 (m, 4H), 6.92-6.84 (m, 4H), 6.21 (d, J=2.4 Hz, 2H), 6.13-6.11 (m, 2H), 3.54 (s, 6H), 3.07 (s, 6H), 2.24 (s, 6H), 2.21 (s, 6H). $^{31}$P NMR (121.5 MHz, CD$_2$Cl$_2$): δ: −14.0 ppm (s).

Example 14

Preparation of (S)-(4, 4, 6, 6'-tetramethoxybiphenyl-2,2'-diyl)bis(bis(4-methylphenyl)phosphine)

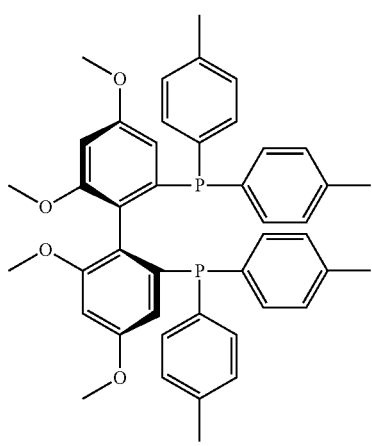

(S)-(4,4',6,6'-tetramethoxybiphenyl-2,2'-diyl)bis(bis(4-methylphenyl)phosphine) was prepared from (S)-(4,4',6,6'-tetramethmbiphenyl-2,2'-diyl)bis(bis(4-methylphenyl)phosphineoxide) using the procedure outlined in Example 13.

Example 15

Preparation of (R)-(4, 4, 6, 6'-tetramethoxybiphenyl-2,2'diyl)bis(bis(3,5-bis(trifluoromethyl)phenyl)phosphine oxide)

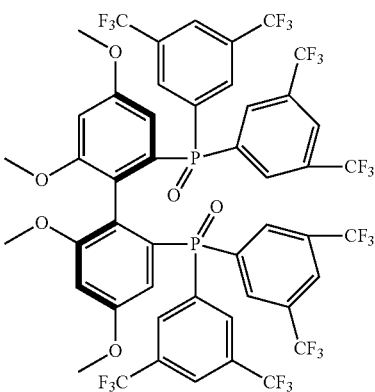

Me$_3$SiCl (0.86 g, 7.4 mmol) was added to a solution of NaI (1.1 g, 7.4 mmol) and (R)-tetraethyl-4,4',6,6'-tetramethoxybiphenyl-2,2'-diyldiphosphonate (1.02 g, 1.83 mmol) in CH$_3$CN (10 ml). The resulting mixture was stirred at 50° C. overnight. All volatiles were removed under vacuum. Dried CH$_2$Cl$_2$ (12 ml) was added to the residues, a few drops of DMF was added followed by oxalyl chloride (2.4 g, 23.8 mmol). The resulting mixture was stirred at 40° C. for 4 h. All volatiles were removed from the filtrate to give the tetrachloride intermediate which was dissolved in THF (30 ml). It was cooled with a dry-ice bath and (3,5-bis(trifluoromethyl)phenyl)magnesium bromide (0.5M in THF, 36 ml, 18 mmol) was added at −78° C. The resulting mixture was stirred at −78° C. for 0.5 h, then was slowly warmed up to RT and stirred for 1 h. NR$_4$Cl (saturated, 30 ml) and water (20 ml) was added to quench the reactions. The organic layer was separated and the aqueous layer was extracted with ethyl acetate (40 ml×1). The combined organic layer was washed with brine (saturated, 80 ml×2) and dried over MgSO$_4$. It was filtered and the solvent was removed from the filtrate to give the crude product as a pale yellow solid which was purified with silica gel chromatography (eluent: CH$_2$Cl$_2$/THF=10/3 to 10/4). The solvent was removed to give the product as a pale yellow solid (1.26 g, 56% yield). $^1$H NMR (300 MHz, CD$_2$Cl$_2$): δ 8.26 (d, J=11.4 Hz, 4H), 8.10 (d, J=11.4 Hz, 4H), 7.99 (d, J=19.2 Hz, 4H), 6.38 (dd, J=2.1 Hz, J=15.6 Hz, 2H), 6.24 (d, J=2.1 Hz, 2H), 3.63 (s, 6H), 3.45 (s, 6H). $^{31}$P NMR (121.5 MHz, CD$_2$Cl$_2$) δ: 23.8 ppm (s).

Example 16

Preparation of (R)-(4,4',6,6'-tetramethoxybiphenyl-2,2'-diyl)bis(bis(3,5-bis(trifluoromethyl)phenyl)phosphine)

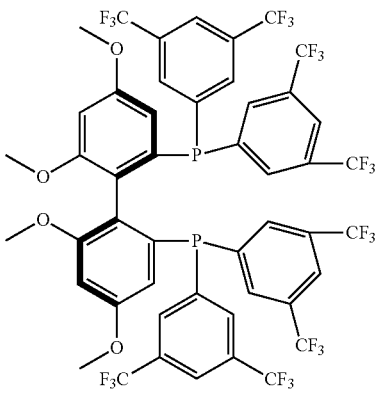

HSiCl$_3$ (1.4 ml) was added to a solution of (R)-(4,4',6,6'-tetramethoxybiphenyl-2,2'-diyl)bis(bis(3,5-ditrifluoromethyl)phenyl)phosphine oxide) (0.50 g, 0.41 mmol) in toluene (40 ml) The mixture was stirred at 110° C. for 36 h (TLC monitored no starting material). It was cooled to RT and NaOH (40 ml, 2M) was added slowly and the mixture stirred for 30 min. The organic layer was separated and the aqueous layer was extracted with toluene (40 ml). The combined organic layer was washed with brine (30 ml), passed through a short silica gel pad (CH$_2$Cl$_2$/Hexane=3/10 as eluent). The solvent was removed from the filtrate and dried under vacuum to give the product as a white solid (0.33 g, 69%). $^1$H NMR (CD$_2$Cl$_2$): δ 7.78 (d, J=26.4 Hz, 4H), 7.58 (d, J=17.1 Hz, 8H), 6.37 (d, J=2.1 Hz, 2H), 6.09-6.07 (m, 2H), 3.56 (s, 6H), 3.31 (s, 6H), $^{31}$P NMR (121.5 MHz, CD$_2$Cl$_2$): δ: −9.32 ppm (s).

Example 17

Preparation of (S)-(4,4',6,6'-tetramethoxybiphenyl-2,2'diyl)bis(bis(3,5-bis(trifluoromethyl)phenyl)phosphine)

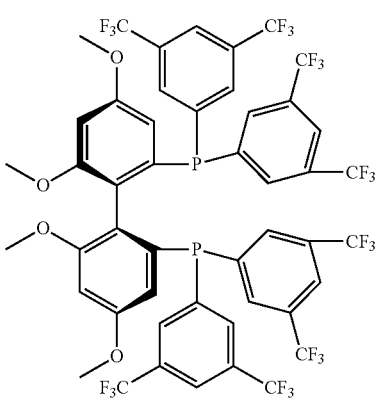

(S)-(4,4',6,6'-tetramethoxybiphenyl-2,2'-diyl)bis(bis(3,5-bis(trifluoromethyl)phenyl) phosphine) was prepared from (S)-(4,4',6,6'-tetramethoxybiphenyl-2,2'-diyl)bis(bis(3,5-bis(trifluoromethyl)phenyl)phosphine oxide) using the procedure outlined in Example 16.

Example 18

Preparation of (3,5-dimethoxyphenyl)diphenylphosphine oxide

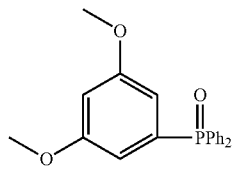

1-Bromo-3,5-dimethoxybenzene (10 g, 46.1 mmol) in THF (60 ml) was added to a Schlenk flask (250 ml) with magnesium (1.2 g, 49.9 mmol), $I_2$ (10 mg) and THF (40 ml). The mixture was reflux for 2 h. It was cooled to RT. The resulting light brown solution was transferred to another flask (250 ml) and it was cooled to −78° C. Chlorodiphenylphosphine (11 g, 49.9 mmol) in THF (30 ml) was added at −78° C. The mixture was stirred at −78° C. for 1 h, then it was slowly warmed up to RT and stirred at RT for 1 h. To the resulting reactions, water (50 ml) was added, then $H_2O_2$ (30%, 13 ml) was added dropwise at 0° C. The resulting mixture was stirred for 30 min. The organic layer was separated and the aqueous layer was extracted with ethyl acetate (50 ml×2). The combined organic layer was washed thoroughly with $NaHSO_3$ (100 ml×3) and brine (100 ml×2) and dried over $MgSO_4$. It was filtered and the solvent was removed to give a viscous oil which was purified with crystallization ($CH_2Cl_2$/Hexane=1:20) to give the product as a colorless solid (15.2 g, Yield: 97.5%). $^1$H NMR (300 Mhz, $CD_2Cl_2$) δ: 7.72-7.64 (m, 4H), 7.60-7.54 (m, 2H), 7.52-7.45 (m, 4H), 6.79 (dd, $J_1$=2.1 Hz, 13.2 Hz, 2H), 6.64 (t, J=2.1 Hz, 1H), 3.77 (s, 6H). $^{31}$P NMR (121.5 MHz, $CD_2Cl_2$) δ: 29.03. $^{13}$C (75 MHz, $CD_2Cl_2$) δ: 161.18 (d, J=17.6 Hz), 135.17 (d, J=102 Hz), 132.99 (d, J=103 Hz), 132.12 (d, J=2.9 Hz), 132.11 (d, J=9.8 Hz), 109.87 (d, J=10.9 Hz), 103.91 (d, J=2.3 Hz), 55.74.

Example 19

Preparation of (2-bromo-3,5-dimethoxyphenyl)diphenylphosphine oxide

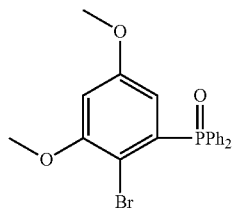

NBS (6.7 g, 37.6 mmol) was added to a solution of (3,5-dimethoxyphenyl)diphenylphosphine oxide (12.3 g, 36.4 mmol) in $CH_2Cl_2$ (140 ml) at 0° C. The resulting suspension was stirred at 0° C. for 1 h. $Na_2CO_3$ (saturated, 40 ml) was added to quench the reactions. It was stirred at RT for 30 min, the organic layer was separated and the aqueous layer was extracted with $CH_2Cl_2$ (40 ml×2). The combined organic layer washed with brine and dried over $MgSO_4$. It was filtered and the solvent was removed to give the crude product as a pale yellow solid (14.3 g, 94% yield). It was sufficiently pure for the next step. The pure sample was obtained by crystallization from $CH_2Cl_2$/Hexane (1/15). $^1$H NMR (300 MHz, $CD_2Cl_2$) δ: 7.73-7.67 (m, 4H), 7.62-7.56 (m, 2H), 7.53-7.46 (m, 4H), 6.69 (d, J=3 Hz, 1H), 6.57 (dd, $J_1$=3 Hz, $J_2$=14.1 Hz, 1H), 3.89 (s, 3H), 3.68 (s, 3H). $^{31}$P NMR (121.5 MHz, $CD_2Cl_2$) δ: 30.72.

Example 20

Preparation of (R,S)-(4,4',6,6'-tetramethoxybiphenyl-2,2'-diyl)bis(diphenylphosphineoxide)

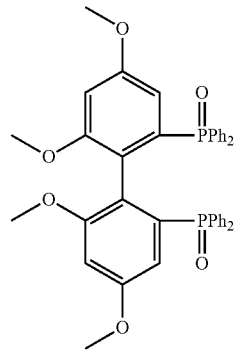

Copper powder (5.81 g, 91.5 mmol) was added to a solution of (2-bromo-3,5-dimethoxyphenyl) diphenylphosphine oxide (12.7 g, 30.5 mmol) in DMF (50 ml). Iodine (100 mg) was added. The resulting suspension was stirred at 140° C. for 2 h. DMF was removed under vacuum. To the residues, $CHCl_3$ (200 ml) was added. It was stirred for 30 min. The solid was filtered and washed with $CHCl_3$ (20 ml). The combined filtrate was washed with brine (with 5% $NH_3.H_2O$, 200 ml×2), brine (20%, 200 ml×1) and dried over $MgSO_4$. The solid was filtered and washed with $CHCl_3$ (20 ml). The solvent was removed from the filtrate to give the crude product as off-white solid which was purified by crystallization from $CH_2Cl_2$/Ether (10/200) to give the pure product as a colorless solid (6.2 g, 60.3% yield).

Example 21

Resolution of (R,S)-(4,4',6,6'-tetramethoxybiphenyl-2,2'-diyl)bis(diphenylphosphineoxide)

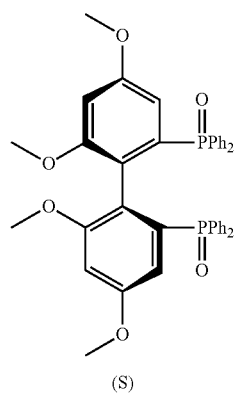

(S)

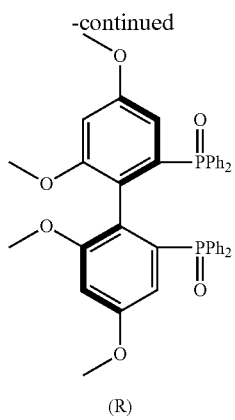

(R)

L-(−)-DBTA monohydrate (3.49 g, 9.28 mmol) in Et₂O (30 ml) was added to the solution of (4,4',6,6'-tetramethoxybiphenyl-2,2'-diyl)bis(diphenylphosphineoxide) (6.2 g, 9.2 mmol) in CH₂Cl₂ (30 ml). Another portion of Et₂O (120 ml) was added to the mixture. The resulting suspension was stirred for 0.5 h. The solid was filtered, washed with ether (20 ml) and dried to give the product as a colorless crystalline solid which was stirred with fresh CH₂Cl₂/Ether (100 ml/150 ml) for 1 h. The white crystalline solid was filtered and it was stirred with another fresh CH₂Cl₂/Ether (80 ml/120 ml) for 1 h. The colorless crystalline solid was filtered and washed with ether (20 ml) and dried under vacuum to give a colorless solid which was suspended in CH₂Cl₂ (150 ml) and washed with NaHCO₃ (saturated, 100 ml×2). The organic layer was dried over MgSO₄. It was filtered and the solvent was removed from the filtrate to give (S)-GarPhos oxide as a colorless solid (2.3 g, 74.2%, 99.5% ee) $[\alpha]^{25}_D$=−115.2° (C=0.95, CH₂Cl₂). The combined mother liquor was neutralized with NaHCO₃ to give the (R)-enriched phosphine oxide (3.9 g) which was resolved with D-(+)-DBTA (2.1 g). The enantiopure product was freed with NaHCO₃ to give the (R)-form enantiomer as a colorless crystalline solid (2.7 g, 87.1% yield, 99.9% ee). $[\alpha]^{25}_D$=+ 114.6° (C=0.99, CH₂Cl₂). (HPLC: Chiralpak IA column 0.46 cm×25 cm. 2-PrOH/Hexane=40/60, 1 ml/min, 25° C., 254 nm. (S)-form=9.55 min, (R)-form=5.88 min).

Example 22

Preparation of (3,5-dimethoxyphenyl)bis(3,5-dimethylphenyl)phosphine oxide

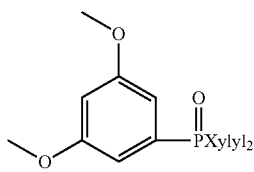

1-Bromo-3,5-dimethoxybenzene (20.2 g, 93 mmol) in THF (80 ml) was added to a flask (500 ml) with magnesium (2.4 g, 99 mmol) and I₂ (20 mg) in THF (100 ml) at 60° C. The mixture was refluxed for 2 h after the addition was completed. It was cooled to RT. The resulting light brown solution was transferred to another flask (250 ml). It was cooled to −78° C. Chlorobis(3,5-dimethylphenyl)phosphine (27.4 g, 99 mmol) in THF (100 ml) was added dropwise at −78° C. within 1 h. The resulting mixture was stirred at −78° C. for 0.5 h, then was slowly warmed up to RT and stirred at RT for 30 min. To the resulting reactions, H₂O (100 ml) was added, then H₂O₂ (25 ml, 30%) was added dropwise at 0° C. The mixture was stirred for 0.5 h at RT. The organic layer was separated and the aqueous layer was extracted with ethyl acetate (100 ml×2). The combined organic layer was washed with brine (200 ml×2), NaHSO₃ (Saturated, 200 ml×3) and dried over MgSO₄. It was filtered and the solvent was removed. The viscous residues were stirred with CH₂Cl₂/Hexane (20 ml/800 ml) for 1 h. The solid was collected by filtration to give the product as a colorless solid (32.3 g, 88% yield). ¹H NMR (300 MHz, CD₂Cl₂) δ: 7.29 (br, 2H), 7.24 (br, 2H), 7.20 (br, 2H), 6.79-6.77 (m, 1H), 6.75-6.73 (m, 1H), 6.63-6.60 (m, 1H), 3.78 (s, 6H), 2.34 (s, 12H). ³¹P NMR (121.5 MHz, CD₂Cl₂) δ: 29.4.

Example 23

Preparation of (2-bromo-3,5-dimethoxyphenyl)bis(3,5-dimethylphenyl)phosphine oxide

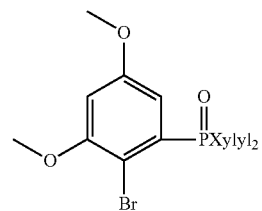

NBS (13.5 g, 76 mmol) was added to a solution of (3,5-dimethoxyphenyl)bis(3,5-dimethylphenyl)phosphine oxide (30 g, 76 mmol) in CH₂Cl₂ (400 ml) at 0° C. The resulting suspension was stirred at 0° C. for 1 h. Na₂CO₃ (saturated, 300 ml) was added to quench the reactions. It was stirred at RT for 30 min and the organic layer was separated. The aqueous layer was extracted with CH₂Cl₂ (100 ml×2). The combined organic layer washed with water (150 ml×2), brine (200 ml×1) and dried over MgSO₄. It was filtered and the solvent was removed to give the crude product as a pale yellow solid (14.3 g) which was sufficiently pure for the next step. The pure product (34.2 g, 93% yield) was obtained by crystallization from ether/Hexane (1/15). ¹H NMR (300 MHz, CD₂Cl₂) δ: 7.32 (br, 2H), 7.28 (br, 2H), 7.21 (br, 2H), 6.67 (d, J=2.7 Hz, 1H), 6.52 (dd, J₁=2.7 Hz, J₂=14.1 Hz, 1H), 3.90 (s, 3H), 3.69 (s, 3H), 2.34 (s, 12H). ³¹P NMR (121.5 MHz, CD₂Cl₂) δ: 31.35.

Example 24

Preparation of (R,S)-(4,4',6,6'-tetramethoxybiphenyl-2,2'-diyl)bis(bis(3,5-dimethylphenyl)phosphine oxide)

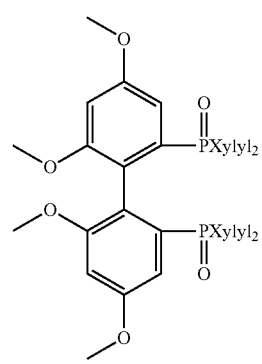

Copper powder (13.5 g, 212.4 mmol) was added to a suspension of (2-bromo-3,5-dimethoxyphenyl)bis(3,5-dimethylphenyl)phosphine oxide (32.6 g, 68.9 mmol) in DMF (180 ml). Iodine (100 mg) was added. The resulting suspension was stirred at 140° C. for 2 h. The DMF was removed under vacuum. To the residues, CHCl$_3$ (300 ml) was added. It was stirred for 30 min. The solid was filtered and washed with CHCl$_3$ (20 ml). The combined filtrate was washed with brine (with 5% NH$_4$OH, 300 ml×2), brine (20%, 300 ml×1) and dried over MgSO$_4$. It was filtered and the solid was washed with CHCl$_3$ (20 ml). The solvent was removed from the filtrate to give the crude product as a off-white solid which was stirred with CH$_2$Cl$_2$/Ether (10 ml/300 ml) for 1 h. The solid was filtered and dried under vacuum to give the pure product as a colorless solid (17.6 g, 64.9% yield). $^1$H NMR (300 MHz, CD$_2$Cl$_2$) δ: 7.37 (d, J=12 Hz, 4H), 7.13 (br, 2H), 7.09 (d, J=13 Hz, 4H), 6.99 (br, 2H), 6.51 (dd, J$_1$=2.4 Hz, J$_2$=14.1 Hz, 2H), 6.20 (d, J=2.4 Hz, 2H), 3.68 (s, 6H), 3.15 (s, 6H), 2.33 (s, 12H), 2.12 (s, 12H). $^{31}$P NMR (121.5 MHz, CD$_2$Cl$_2$) δ: 30.08.

Example 25

Resolution of (R,S)-(4,4',6,6'-tetramethoxybiphenyl-2,2'diyl)bis(bis(3,5-dimethylphenyl)-phosphine oxide)

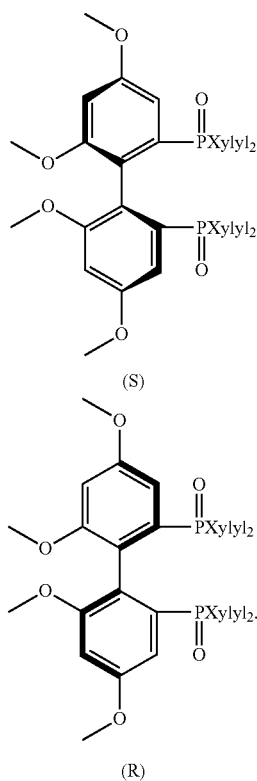

L-(−)-DBTA monohydrate (7.9 g, 21 mmol) in Et$_2$O (130 ml) was added to the solution of (4,4',6,6'-tetramethoxybiphenyl-2,2'-diyl)bis(bis(3,5-dimethylphenyl)phosphine oxide) (16 g, 20.3 mmol) in CH$_2$Cl$_2$ (75 ml). CCl$_4$ (150 ml) was added, then another portion of Et$_2$O (580 ml) was added to the mixture. The resulting mixture was stirred for 1 h. The solid was filtered, washed with ether (50 ml) and dried to give the product as a colorless crystalline solid (17.6 g) which was stirred with fresh CH$_2$Cl$_2$ (100 ml) for 15 min, then 001$_4$ (155 ml) was added and the mixture was stirred for another 15 min. Ether (480 ml) was added dropwise. The resulting suspension was stirred for another 40 min. The crystalline solid was filtered, washed with ether (40 ml) and dried under vacuum to give the product as a colorless solid (11.5 g) which was suspended in CH$_2$Cl$_2$ (80 ml) and washed with NaHCO$_3$ (saturated, 100 ml×2). The organic layer was dried over MgSO$_4$. It was filtered and the solvent was removed from the filtrate to give the (R)-form of the enantiomer as a colorless solid (7.4 g, 92.5% yield, >99% ee). [α]=+185.9° (C=0.71, CH$_2$Cl$_2$). The combined mother liquor was neutralized with NaHCO$_3$ to give the (S)-enriched phosphine oxide (8.5 g) which was resolved with D-(+)-DBTA (4.0 g). The enantiopure complex was freed with NaHCO$_3$ to give the (S)-form enantiomer as a colorless solid (7.6 g, 95% yield, >99% ee). [α]$_D^{25}$=−186.3° (C=1.01, CH$_2$Cl$_2$). (HPLC: Chiralpak IA column 0.46 cm×25 cm. 2-PrOH/Hexane (1% Et$_2$NH)=5/95, 1 ml/min, 25° C., 254 nm. (S)-form=19.10 min, (R)-form=25.90 min).

Example 26

Preparation of (R)-(4,4',6,6'-tetramethoxybiphenyl-2,2'diyl)bis(bis(3,5-dimethylphenyl)phosphine

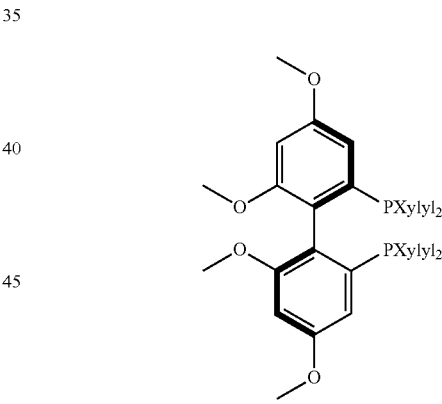

HSiCl$_3$ (4.0 ml) was added to the solution of (R)-(4,4',6,6'-tetramethoxybiphenyl-2,2'-diyl)bis(bis(3,5-dimethylphenyl)phosphine oxide) (1.1 g, 1.4 mmol) in toluene (60 ml). The resulting mixture was stirred at 110° C. overnight under Ar. It was cooled to RT and NaOH (2N, 100 ml) was added slowly under 0° C. The resulting mixture was stirred RT for 30 min. The organic layer was separated and the aqueous layer was extracted with toluene (60 ml×1). The combined organic layer was washed with brine and dried over MgSO$_4$. It was filtered though a silica gel pad. The solvent was removed to give the product as a white solid (1.03 g, 97.6%). $^1$H NMR (300 MHz, CD$_2$Cl$_2$) δ: 6.95 (s, 2H), 6.91-6.89 (m, 4H), 6.86 (s, 2H), 6.72-6.70 (m, 4H), 6.37-6.36 (m, 2H), 6.31-6.29 (m, 2H), 3.66 (s, 6H), 3.25 (s, 6H), 2.27 (s, 12H), 2.16 (s, 12H). $^{31}$P NMR (121.1 MHz, CD$_2$Cl$_2$) δ: −12.54.

Example 27

Preparation of (S)-(4,4',6,6'-tetramethoxybiphenyl-2,2'-diyl)bis(bis(3,5-dimethylphenyl)phosphine

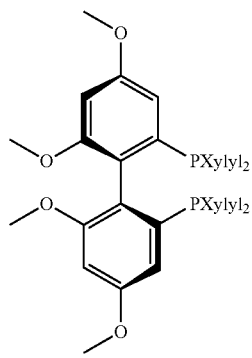

(S)-(4,4',6,6'-tetramethoxybiphenyl-2,2'-diyl)bis(bis(3,5-dimethylphenyl)phosphine was prepared from (S)-(4,4',6,6'-tetramethoxybiphenyl-2,2'-diyl)bis(bis(3,5-dimethylphenyl)phosphine oxide) using the procedure outlined in Example 26.

Example 28

Preparation of (3,5-dimethoxyphenyl)bis(4-methoxy-3,5-dimethylphenyl)phosphine oxide

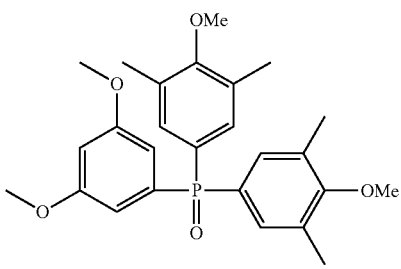 [SMILES: COc1cc(OC)cc(P(=O)(c2cc(C)c(OC)c(C)c2)c2cc(C)c(OC)c(C)c2)c1]

1-Bromo-3,5-dimethoxybenzene (10 g, 46.1 mmol) in THF (60 ml) was added to a flask (250 ml) with magnesium (1.2 g, 49.9 mmol) and $I_2$ (20 mg) in THF (40 ml) at 60° C. The mixture was refluxed for 2 h after the addition was completed. It was cooled to RT. The resulting light brown solution was transferred to another flask (250 ml). It was cooled to −78° C. and chlorobis(4-methoxy-3,5-dimethylphenyl)phosphine (16.8 g, 49.9 mmol) in THF (40 ml) was added dropwise at −78° C. within 1 h. The resulting mixture was stirred at −78° C. for 0.5 h, then slowly warmed up to RT and stirred at RT for 30 min. To the resulting mixture water (50 ml) was added, then $H_2O_2$ (13 ml) was added dropwise at 0° C. The mixture was stirred for 0.5 h at RT. The organic layer was separated and the aqueous layer was extracted with ethyl acetate (100 ml×2) and $CH_2Cl_2$ (100 ml×1). The combined organic layer was washed with brine (200 ml×2), $NaHSO_3$ (200 ml×3) and dried over $MgSO_4$. It was filtered and the solvent was removed. The viscous residues were stirred with $CH_2Cl_2$/hexane (5 ml/100 ml) for 1 h. The solid was collected by filtration to give the product as a colorless solid (17.4 g, 83 yield). $^1H$ NMR (300 MHz, $CD_2Cl_2$) δ: 7.32 (s, 2H), 7.28 (s, 2H), 6.76 (dd, J=2.4 Hz, J=12.9 Hz, 2H), 6.61 (t, J=2.4 Hz, 1H), 3.78 (s, 6H), 3.75 (s, 6H), 2.28 (s, 12H). $^{31}P$ NMR (121.5 MHz, $CD_2Cl_2$) δ: 28.4.

Example 29

Preparation of (2-bromo-3,5-dimethoxyphenyl)bis(4-methoxy-3,5-dimethylphenyl)phosphine oxide

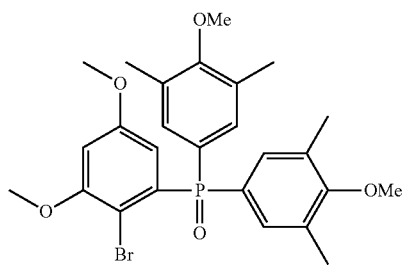 [SMILES: COc1cc(OC)c(Br)c(P(=O)(c2cc(C)c(OC)c(C)c2)c2cc(C)c(OC)c(C)c2)c1]

NBS (4.5 g, 25.3 mmol) was added to a solution of (3,5-dimethoxyphenyl)bis(3,5-dimethylphenyl)phosphine oxide (11.3 g, 25 mmol) in $CH_2Cl_2$ (150 ml) at 0° C. The resulting suspension was stirred at 0° C. for 1 h. $Na_2CO_3$ (saturated, 60 ml) was added to quench the reaction. It was stirred at RT for 30 min and the organic layer was separated and the aqueous layer was extracted with $CH_2Cl_2$ (40 ml×2). The combined organic layer was washed with water (150 ml×2), brine (200 ml×1) and dried over $MgSO_4$. It was filtered and the solvent was removed to give the crude product as a pale yellow solid (12.9 g) which was sufficiently pure for the next step. The pure product (12.0 g, 90% yield) was obtained by silica gel chromatograpy. $^1H$ NMR (300 MHz, $CD_2Cl_2$) δ: 7.35 (s, 2H), 7.31 (s, 2H), 6.67 (d, J=2.7 Hz, 1H), 6.59 (dd, J=2.7 Hz, J=14.1 Hz, 1H), 3.90 (s, 3H), 3.76 (s, 6H), 3.71 (s, 3H), 2.29 (s, 12H). $^{31}P$ NMR (121.5 MHz, $CD_2Cl_2$) δ: 30.4.

Example 30

Preparation of (R,S)-(4,4',6,6'-tetramethoxybiphenyl-2,2'-diyl)bis(bis(4-methoxy-3,5-dimethylphenyl)phosphine) oxide

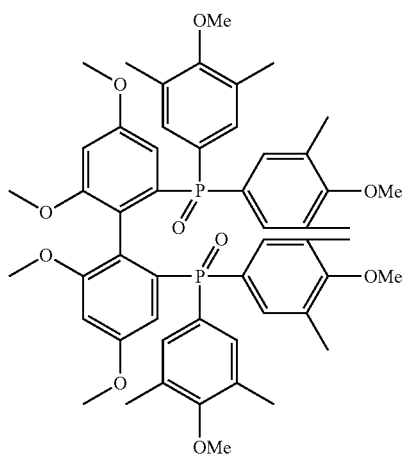 [SMILES: COc1cc(OC)c(-c2c(OC)cc(OC)cc2P(=O)(c2cc(C)c(OC)c(C)c2)c2cc(C)c(OC)c(C)c2)c(P(=O)(c2cc(C)c(OC)c(C)c2)c2cc(C)c(OC)c(C)c2)c1]

Copper powder (3.6 g, 56.6 mmol) was added to a solution of (2-bromo-3,5-dimethoxyphenyl)bis(4-metoxy-3,5-dimethylphenyl)phosphine oxide (10 g, 18.7 mmol) in DMF (30 ml) and iodine (20 mg) was added. The resulting suspension was stirred at 140° C. for 2 h. DMF was removed under vacuum. To the residues, CHCl₃ (50 ml) was added. It was stirred for 30 min. The solid was filtered and washed with CHCl₃ (20 ml). The combined filtrate was washed with brine (with 5% NH₃H₂O, 100 ml×2), brine (20%, 100 ml×1) and dried over MgSO₄. It was filtered and the solid was washed with CHCl₃ (20 ml). The solvent was removed from the filtrate to give the crude product as a tan solid (7.8 g). It was purified by recrystallization from ether/hexane (30 ml/50 ml). The solid was filtered and dried under vacuum to give the pure product as a pale yellow solid (4.5 g, 53% yield). $^1$H NMR (300 MHz, CD₂Cl₂) δ: 7.42 (d, J=11.4 Hz, 4H), 7.14 (d, J=11.4 Hz, 4H), 6.54 (dd, J=14.4 Hz, J=2.4 Hz, 2H), 6.18 (d, J=2.4 Hz, 2H), 3.74 (s, 6H), 3.69 (s, 6H), 3.68 (s, 6H), 3.17 (s, 6H), 2.27 (s, 12H), 2.07 (s, 12H). $^{31}$P NMR (121.5 MHz, CD₂Cl₂) δ: 29.1.

Example 31

Resolution of (R,S)-(4,4',6,6'-tetramethoxybiphenyl-2,2'-diyl)bis(bis(4-methoxy-3,5-dimethylphenyl)phosphine) oxide

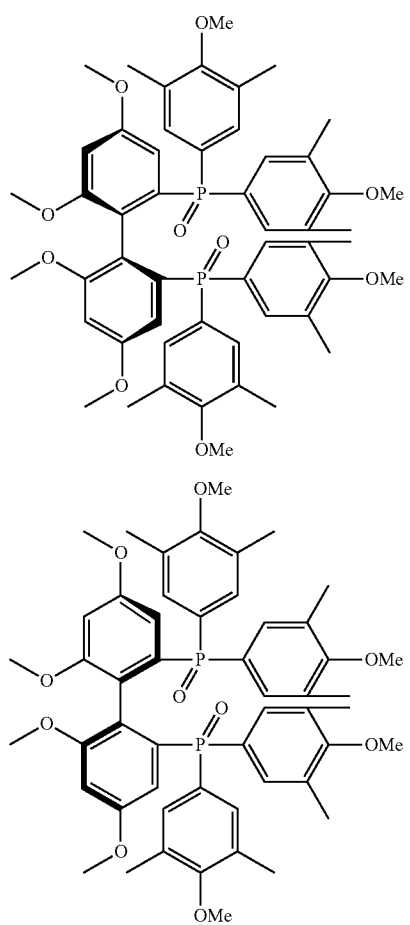

L-(−)-DBTA monohydrate (1.08 g, 2.87 mmol) in Et₂O (25 ml) was added to a solution of (4,4',6,6'-tetramethoxybiphenyl-2,2'-diyl)bis(bis(4-methoxy-3,5-dimethylphenyl)phosphine) oxide (4.5 g, 4.96 mmol) in CH₂Cl₂ (17 ml). CCl₄ (20 ml) was added, then another portion of Et₂O (120 ml) was added to the mixture. The resulting mixture was stirred for 0.5 h. The solid was collected by filtration and was washed with ether (15 ml) and dried to give the product as a colorless crystalline solid (3.3 g) which was stirred with fresh CH₂Cl₂/CCl₄/Et₂O (15 ml/15 ml/100 ml) for 40 min. The crystalline solid was filtered, washed with ether (15 ml) and dried under vacuum to give a colorless solid (3.1 g) which was dissolved in CH₂Cl₂ (40 ml) and washed with NaHCO₃ (saturated, 40 ml×2). The organic layer was dried over MgSO₄. It was filtered and the solvent was removed from the filtrate to give the (R)-form enantiomer as a colorless solid (2.0 g, 90% yield, >99% ee). $[\alpha]^{25}_D$=+ 150.6° (C=1.0, CH₂Cl₂). The combined mother liquor was free with NaHCO₃ to give enriched phosphine oxide which was resolved with D-(+)-DBTA as before. The enatiopure complex was free with NaHCO₃ to give (S)-form enantiomer as colorless solid (2.04 g, 91.8% yield, >99% ee). $[\alpha]^{25}_D$=−156.0° (C=1.01, CH₂Cl₂). (HPLC: Chiralpak IA column 0.46 cm×25 cm. 2-PrOH/Hexane (0.5% Et₂NH)=8/92, 1 ml/min, 25° C., 254 nm. (S)-form=15.8 min, (R)-form=22.9 min).

Example 32

Preparation of (R)-(4,4',6,6'-tetramethoxybiphenyl-2,2'-diyl)bis(bis(4-methoxy-3,5-dimethylphenyl)phosphine)

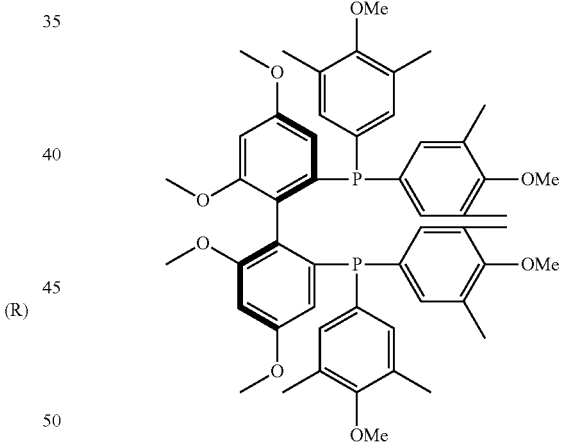

HSiCl₃ (4.0 ml, 5.4 g, 39.9 mmol) was added to a solution of (R)-(4,4',6,6'-tetramethoxybiphenyl-2,2'-diyl)bis(bis(4-methoxy-3,5-dimethylphenyl)phosphine) oxide (2.0 g, 2.2 mmol) in toluene (75 ml). The resulting suspension was stirred at 120° C. for 6 h under Ar. It was cooled to RT and NaOH (4N, 80 ml) was added slowly at 0° C. The resulting mixture was stirred at RT for 30 min. The organic layer was separated and the aqueous layer was extracted with toluene (80 ml×1). The combined organic layer was washed with brine and dried over MgSO₄. It was filtered though a silica gel pad and was washed with CH₂Cl₂/THF (10/1, 50 ml). The solvent was removed to give the product as a white solid (1.83 g, 95%). $^1$H NMR (300 MHz, CD₂Cl₂) δ: 6.93-6.92 (m, 4H), 6.82-6.80 (m, 4H), 6.34-6.31 (m, 4H), 3.70 (s, 6H), 3.67 (s, 12H), 3.24 (s, 6H), 3.23 (s, 12H), 3.14 (s, 12H). $^{31}$P NMR (121.1 MHz, CD$_2$Cl$_2$) δ: −13.87.

Example 33

Preparation of (S)-(4,4',6,6'-tetramethoxybiphenyl-2,2'diyl)bis(bis(4-methoxy-3,5-dimethylphenyl)phosphine)

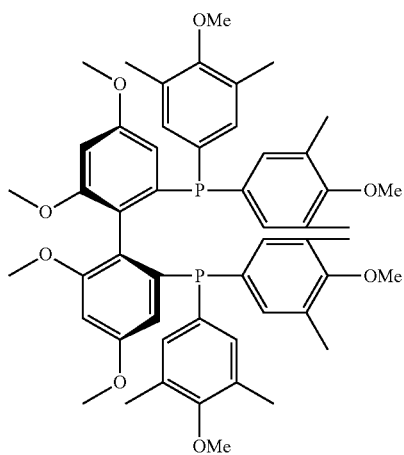

(S)-(4,4',6,6'-tetramethoxybiphenyl-2,2'-diyl)bis(bis(4-methoxy-3,5-dimethyl-phenyl)phosphine) was prepared from (S)-(4,4',6,6'-tetramethoxybiphenyl-2,2'-diyl)bis(bis(4-methoxy-3,5-dimethylphenyl)phosphine) oxide using the procedure outlined in Example 32.

Example 34

General procedure for preparation of RuCl$_2$(p-cymene)(Diphosphine) catalysts

A cosolvent of ethanol/CH$_2$Cl$_2$ (3/1, 40 ml) was added to the mixture of [RuCl$_2$(p-cymene)]$_2$ (0.25 mmol) and the diphosphine ligand (0.5 mmol). The mixture was refluxed under an inert atmosphere for 3-5 h. All volatiles were removed under vacuum. CH$_2$Cl$_2$ (4 ml) was added to dissolve the residues, and hexane (20 ml) was added to precipitate any impurities. The mixture was filtered and the filtrate was concentrated to give the product as a yellow solid. Yield=80-85%.
(a) RuCl$_2$(p-cymene)((R)-Ph-Garphos): $^{31}$P NMR (121.5 MHz, CD$_2$Cl$_2$) δ: 42.6 ppm (d, J=62.7 Hz); 29.0 ppm (d, J=62.7 Hz).
(b) RuCl$_2$(p-cymene)((R)-DMM-Garphos): $^{31}$P NMR (162.0 MHz, CD$_2$Cl$_2$) δ: 39.3 ppm (d, J=62.9 Hz); 27.1 ppm (d, J=62.9 Hz).

Example 35

General Procedure for Preparation of RuCl$_2$(Diphosphine)(Diamine) catalysts

A cosolvent of Toluene and DMF (10 ml/0.5 ml) was added to a mixture of the diphosphine ligand (1.0 mmol) and [RuCl$_2$(cymene)]$_2$ (320 mg, 0.5 mmol). The resulting mixture was stirred at 70° C. for 2 h. It was cooled to RT and the chiral diamine (1.04 mmol) was added to the mixture. The reactions were stirred at 70° C. for another 1.5 h. All volatiles were removed under vacuum to give product as a brown of yellow solid. Yield=95-99%.
(a) RuCl$_2$ ((S)-Ph-Garphos)((S,S-DPEN): $^{31}$P NMR (162.0 MHz, CD$_2$Cl$_2$) δ: 48.01 ppm (s).
(b) RuCl$_2$ ((S)-Ph-Garphos)((S)-DAIPEN): $^{31}$P NMR (162.0 MHz, CD$_2$Cl$_2$) δ: 50.55 ppm (d); 49.32 ppm (d).
(c) RuCl$_2$ ((S)-Xylyl-Garphos)((S,S-DPEN): $^{31}$P NMR (162.0 MHz, CD$_2$Cl$_2$) δ: 46.8 ppm (s).
(d) RuCl$_2$ ((R)-Xylyl-Garphos)((R)-DAIPEN): $^{31}$P NMR (162.0 MHz, CD$_2$Cl$_2$) δ: 49.1 ppm (d); 48.3 ppm (d). The x-ray crystal structure of this catalyst is shown in FIG. 1.
(e) RuCl$_2$ ((S)-Xylyl-Garphos)((S)-DAIPEN): $^{31}$P NMR (162.0 MHz, CD$_2$Cl$_2$) δ: 49.1 ppm (d); 48.3 ppm (d).
(f) RuCl$_2$ ((S)-DMM-Garphos)((S,S-DPEN): $^{31}$P NMR (121.5 MHz, CD$_2$Cl$_2$) δ: 45.5 ppm (s).
(g) RuCl$_2$ ((S)-DMM-Garphos)((S)-DAIPEN): $^{31}$P NMR (121.5 MHz, CD$_2$Cl$_2$) δ: 48.0 ppm (d); 47.6 ppm (d).

Example 36

General Procedure for Preparation of [Rh(COD)(diphosphine)][BF$_4$] Catalysts

A solution of HBF$_4$.Et$_2$O (0.5 g, 3.1 mmol) in THF (5 ml) was added to the solution of Rh(COD)(acac) (0.93 g, 3.0 mmol) in THF (30 ml). The mixture was stirred at 50° C. for 1 h. It was cooled to RT and the chiral diphosphine (3.0 mmol) was added. The resulting orange solution was stirred at 50° C. for another 1 h. All volatiles were removed under vacuum to give the crude product as an orange solid. Ether (30 ml) was added to the residues. The suspension was stirred at RT for 2 h. It was filtered and dried under vacuum to give the pure product as an orange solid. Yield=90-95%.
(a) [Rh(COD)((R)-Ph-Garphos)][BF$_4$]: $^{31}$P NMR (121.5 MHz, CD$_2$Cl$_2$) δ: 26.3 ppm (d, J=145.8 Hz).
(b) [Rh(COD)((R)-Xylyl-Garphos)][BF$_4$]: $^{31}$P NMR (121.5 MHz, CD$_2$Cl$_2$) δ: 26.2 ppm (d, J=144.7 Hz).
(c) [Rh(COD)((R)-DMM-Garphos)][BF$_4$]: $^{31}$P NMR (121.5 MHz, CD$_2$Cl$_2$) δ: 24.8 ppm (d, J=145.2 Hz).

Example 37

Hydrogenation of ethyl 4-chloroacetoacetate using RuCl$_2$(p-cymene)-(R-Ph-Garphos)

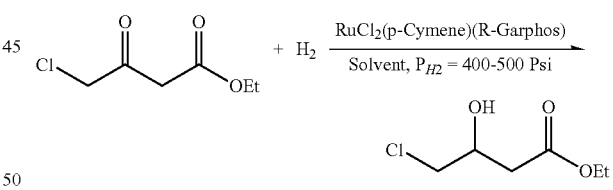

A solution of the catalyst in methylene chloride was added to a solution of the substrate in a 50 ml autoclave under argon. The mixture was purged with hydrogen gas, heated to the desired temperature and pressurized with hydrogen. After stirring for the desired time, the autoclave was cooled to room temperature and vented. The conversion was assayed by GC. A sample of the product was converted to the ethyl ester and the enantioselectivity was determined using GC.

Example 38

Hydrogenation of Simple Ketones Using RuCl$_2$(Garphos)(Diamine) as Catalyst

A solution of the ketone in 2-propanol was added to a 50 mL Schlenk flask. After evacuating and refilling with argon, a mixture of the catalyst and base (eg. KO'Bu) was added. The resulting mixture was then injected into a 50 mL autoclave which had been previously placed under an atmosphere of hydrogen. The autoclave was pressurized with hydrogen gas and the reaction mixture was stirred at the desired temperature. The reaction progress was monitored by TLC. Upon completion of the reaction, the solvent was removed under vacuum and the mixture was filtered through a short pad of silica gel (ca. 6 cm) using hexane/ethyl acetate. The solvent was then removed from the filtrate affording the product.

Example 39

Hydrogenation of 1-(3,5-bis(trifluoromethyl)phenyl)ethanone using RuCl$_2$(Garphos)(Diamine) as catalyst A mixture of the ketone and KO'Bu in 2-propanol was stirred under hydrogen gas for 5 minutes in a 50 mL autoclave. A solution of the catalyst in 2-propanol was degassed with argon and then injected into the autoclave. This was then pressurized with hydrogen gas and the reaction mixture was stirred at the desired temperature. The reaction progress was monitored by TLC. Upon completion of the reaction, the solvent was removed under vacuum and the mixture was filtered through a short pad of silica gel (ca. 6 cm) using 3:1 hexane:ethyl acetate. The solvent was then removed from the filtrate affording the product.

Example 40

Hydrogenation of (E)-methyl 2-(3-(3-(2-(7-chloroquinolin-2-yl)vinyl)phenyl)-3-oxopropyl)benzoate

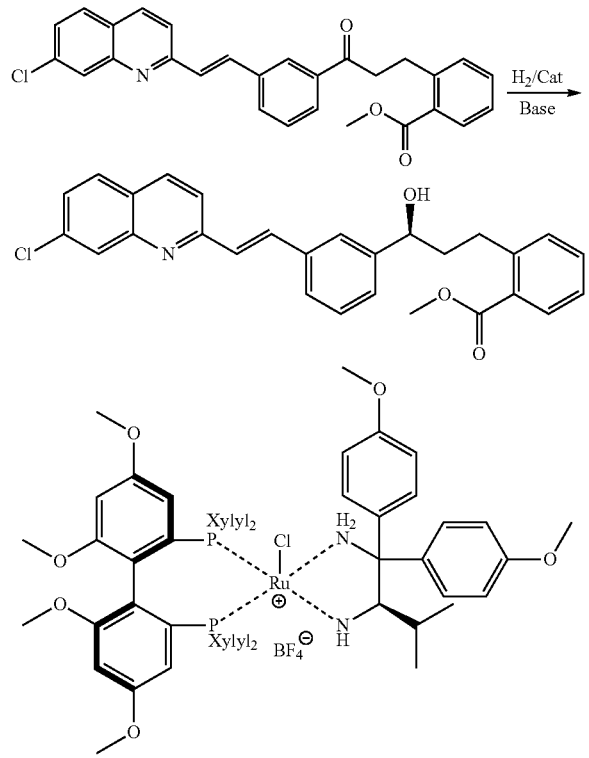

The substrate (0.2 g), Tetrabutylammonium bromide (7.0 mg), Toluene (5 ml) and NaOH (1M, 0.5 ml) were combined in a stainless steel autoclave. The autoclave was sealed and repeatedly pressurized and vented with hydrogen gas to ensure complete exchange of the atmosphere within the autoclave under stirring. An aliquot (1.0 ml) of a stock solution of catalyst (prepared under Argon by dissolving 2.2 mg catalyst in 4.0 ml 2-PrOH) was added to the autoclave. The autoclave was then pressurized and vented with hydrogen 3-5 times to purge the atmosphere of any residual air. The hydrogenation was effected at ambient temperature under 130 Psi for 24 hours. The NMR analysis of an aliquot (removed from the autoclave after appropriately venting any residual pressure) revealed full conversion. The pure sample for HPLC was obtained by silica gel chromatography (eluent: CH$_2$Cl$_2$/THF=1/20). The e.e. (>99%) was determined by HPLC: Chiral column: Chiralpak AS-H column 0.46 cm×25 cm; HPLC Condition: column temperature=40° C.; 2-PrOH/hexanes=10/90, 1.0 ml/min; Retention time for R-isomer=17.8 min, for S-isomer=22.4 min, starting material=13.5 min.

Example 41

Preparation of DTBM-Garphos a) Preparation of bis(3,5-di-tert-butyl-4-methoxyphenyl)(3,5-dimethoxyphenyl)phosphine oxide

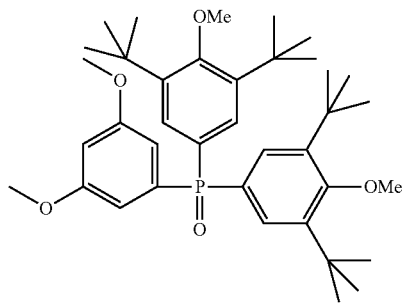 [SMILES: COc1cc(OC)cc(P(=O)(c2cc(C(C)(C)C)c(OC)c(C(C)(C)C)c2)c2cc(C(C)(C)C)c(OC)c(C(C)(C)C)c2)c1]

1-Bromo-3,5-dimethoxybenzene (25.5 g, 117.5 mmol) in THF (150 mL) was added to a mixture of magnesium (3.14 g, 129.2 mmol) and iodine (120 mg) in THF (100 mL). The mixture was refluxed for 1 hour after the addition was completed. It was cooled to RT. The resulting light brown solution was transferred to another flask. It was cooled to −78° C. and chlorobis(3,5-di-tert-butyl-4-methoxyphenyl)phosphine (59.3 g, 117.4 mmol) in THF (100 mL) was added dropwise at −78° C. The resulting mixture was stirred at −78° C. for 0.5 h, then slowly warmed up to RT and stirred at RT for 1 hour. To the resulting mixture water (300 mL) was added, then H$_2$O$_2$ (17 mL, 30%) was added dropwise at 0° C. The mixture was stirred for 30 minutes. The organic layer was separated and the aqueous layer was extracted with ethyl acetate (200 mL×2) and CH$_2$Cl$_2$ (200 mL×1). The combined organic layer was washed with brine (200 mL×2), NaHSO$_3$ (200 mL×3) and dried over MgSO$_4$. It was filtered and the solvent was removed. The viscous residue was dissolved in CH$_2$Cl$_2$ (30 mL) and ether (100 mL), then hexane (400 mL) added. The mixture was concentrated to 400 mL under reduced pressure and then seeded. The suspension was stirred for 1.5 hour and the resulting solid was collected by filtration and dried to give the product as a colorless solid (57 g). a second crop (13 g) was collected from the mother liquor. Yield=95.7%. $^1$H NMR (300 MHz, CDCl$_3$) δ: 7.47 (d, J=12.6 Hz, 4H), 6.83 (dd, J$_1$=12.6 Hz, J$_2$=2.1 Hz, 2H), 6.60 (t, J=2.1 Hz, 2H), 3.78 (s, 6H), 3.68 (s, 6H), 1.35 (s, 36H). $^{31}$P NMR (121.5 MHz, CDCl$_3$) δ: 32.9.

b) Preparation of (2-bromo-3,5-dimethoxyphenyl)bis (3,5-di-tert-butyl-4-methoxyphenyl)phosphine oxide

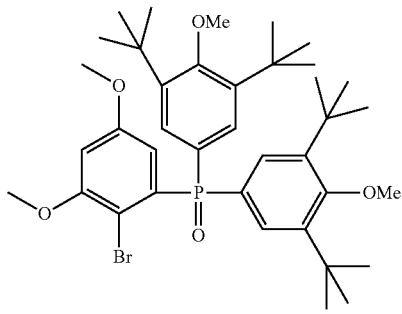 [SMILES: COc1cc(OC)c(Br)c(P(=O)(c2cc(C(C)(C)C)c(OC)c(C(C)(C)C)c2)c2cc(C(C)(C)C)c(OC)c(C(C)(C)C)c2)c1]

NBS (206 g, 115.7 mmol) was added to a solution of bis(3,5-di-tert-butyl-4-methoxyphenyl)(3,5-dimethoxyphenyl)phosphine oxide (70 g, 112.4 mmol) in CH$_2$Cl$_2$ (350 mL) at 0° C. The resulting suspension was stirred at 0° C. for 1 h then was warmed to RT and stirred for 4 h. The reaction was monitored by TLC until no starting material remained. The solution was washed with conc. Na$_2$CO$_3$ (300 mL×2) at RT. The organic layer was separated and dried over MgSO$_4$. It was filtered and the solvent was removed to give the crude product. Hexane (400 mL) was added and the solution concentrated to 300 mL. It became cloudy and a white solid precipitated. Another 100 mL of hexane was added. The suspension was stirred at RT for 2 h. It was filtered and the solid dried under vacuum to give the product as a colourless solid (64.4 g). A second crop (7.2 g) was obtained from the mother liquor. Overall yield=90.9%. $^1$H NMR (400 MHz, CDCl$_3$) δ: 7.55 (d, J=13.2 Hz, 4H), 7.04 (dd, J$_1$=13.2 Hz, J$_2$=2.8 Hz, 1H), 6.65 (d, J=2.8 Hz, 1H), 3.88 (s, 3H), 3.77 (s, 3H), 3.68 (s, 6H), 1.36 (s, 36H). $^{31}$P NMR (162.0 MHz, CDCl$_3$) δ: 32.4.

c) Preparation of (R,S)-(4,4',6,6'-tetramethoxybiphenyl-2,2'-diyl)bis(bis(3,5-di-tert-butyl-4-methoxyphenyl)phosphine) oxide

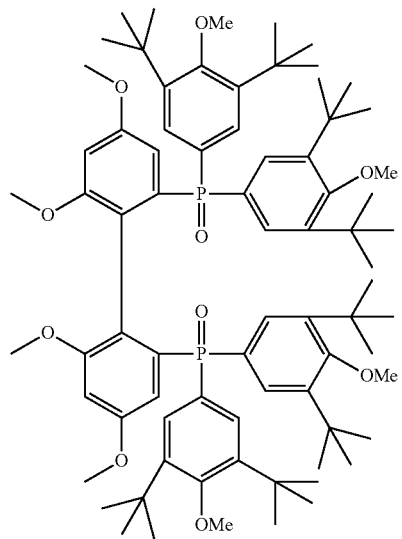 [SMILES: COc1cc(OC)c(-c2c(OC)cc(OC)cc2P(=O)(c2cc(C(C)(C)C)c(OC)c(C(C)(C)C)c2)c2cc(C(C)(C)C)c(OC)c(C(C)(C)C)c2)c(P(=O)(c2cc(C(C)(C)C)c(OC)c(C(C)(C)C)c2)c2cc(C(C)(C)C)c(OC)c(C(C)(C)C)c2)c1]

Iodine (320 mg) was added to a mixture of copper powder (19.2 g, 302 mmol) and (2-bromo-3,5-dimethoxyphenyl)bis (3,5-di-tert-butyl-4-methoxyphenyl)phosphine oxide (70.5 g, 105 mmol) in DMF (300 mL). The resulting suspension was stirred at 140° C. for 3.5 h. It was filtered and the solids washed with DMF (40 mL). The combined filtrate was transferred to a 2 L round bottom flask, water was added and the suspension stirred for 1 hour. It was filtered and the solids were dissolved in CH$_2$Cl$_2$ and washed with NH$_4$OH solution (3%, 500 mL×3), then water (500 mL). The organic layer was dried over MgSO$_4$. It was filtered and the solid was washed with CHCl$_3$ (20 mL). The solvent was removed to give a viscous oil which was crystallized from ether/hexane (1/10, 500 mL) to give a mixture of the coupled product and debromination product (1:1, 65 g). This was washed with ethyl acetate/hexane (150 mL/150 mL) to give the pure product as a colourless solid. Yield=32.8 g. $^1$H NMR (400 MHz, CDCl$_3$) δ: 7.55 (d, J=12.0 Hz, 4H), 7.50 (d, J=12.0 Hz, 4H), 6.39 (d, J=2.0 Hz, 2H), 6.33 (dd, J=14.0 Hz, J$_2$=2.0 Hz, 2H), 3.66 (s, 6H), 3.64 (s, 6H), 3.60 (s, 6H), 3.05 (s, 6H), 1.36 (s, 36H), 1.29 (s, 36H). $^{31}$P NMR (162.0 MHz, CDCl$_3$) δ: 29.3. The debrominated byproduct (31 g) was also recovered.

d) Resolution of (R,S)-(4,4',6,6'-tetramethoxybiphenyl-2,2'-diyl)bis(bis(3,5-di-tert-butyl-4-methoxyphenyl)phosphine) oxide

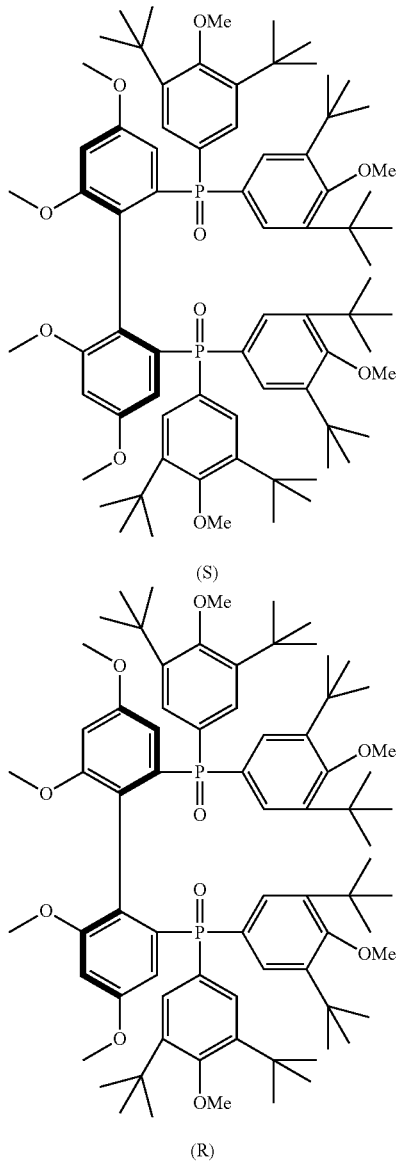

A sample of (R,S)-(4,4',6,6'-tetramethoxybiphenyl-2,2'-diyl)bis(bis(3,5-di-tert-butyl-4-methoxyphenyl)phosphine) oxide (32.8 g, 26.4 mmol) was suspended in diethylether (285 mL) and ethyl acetate (100 mL). Then L-(−)-DBTA monohydrate (9.92 g, 26.4 mmol) was added. The mixture was stirred at RT and it changed from clear to cloudy. A white solid precipitated. Ethyl acetate (180 mL) was added. The suspension was stirred for 1 hour. It was filtered and the solid was washed with ethyl acetate (25 mL) and dried under vacuum to give 18 g of product. The solid was suspended and stirred in another portion of ethyl acetate/ether (90 mL/90 mL) for 1 hour. It was filtered and the solid washed with ethyl acetate (20 mL) and dried to give pure (S)-DTBM-Garphos oxide/(−)-DBTA complex as a colourless solid (13.4 g). The free (S)-DTBM-Garphos oxide was liberated using Na$_2$CO$_3$ solution and was isolated as a colourless solid. Yield=10.3 g.

The solvent was removed from the mother liquor (above) and (+)-DBTA (5.8 g, 16.2 mmol) was added to a suspension of the solid in ether (120 mL) and EA (50 mL). It was stirred for several minutes and ethyl acetate (70 mL) was added slowly. The resulting suspension was stirred overnight. The solid was filtered and washed with ether (30 mL). It was dried to give the (R)-DTBM-Garphos oxide/(+)-DBTA complex as a colourless solid (17.1 g) which was dissolved in CH$_2$Cl$_2$ (150 mL) and stirred with Na2CO3 solution to liberate the free phosphine. Workup gave the (R)-DTBM-Garphos oxide as a colourless solid. Yield=13.0 g (>99% ee). [α]$^{25}_D$=+82.8° (C=1.0, CH$_2$Cl$_2$).

e) Preparation of (R)-(4,4',6,6'-tetramethoxybiphenyl-2,2'-diyl)bis(bis(3,5-di-tert-butyl-4-methoxyphenyl)phosphine)

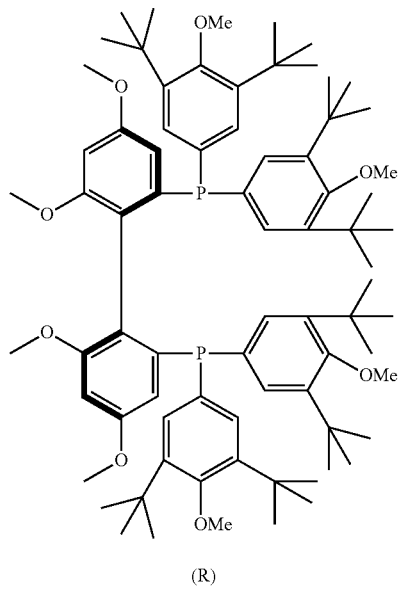

(R)

HSiCl$_3$ (14.2 g, 105 mmol) was added to a solution of (R)-(4,4',6,6'-tetramethoxybiphenyl-2,2'-diyl)bis(bis(3,5-di-tert-butyl-4-methoxyphenyl)-phosphine) oxide (13.0 g, 10.5 mmol) in toluene (150 mL). The resulting suspension was stirred at 100° C. overnight. It was cooled to RT and NaOH (2M, 300 mL) was added slowly at 0° C. The resulting mixture was stirred at RT for 30 min. The organic layer was separated and the aqueous layer was extracted with toluene (2×150 mL). The combined organic layer was evaporated to dryness and CH$_2$Cl$_2$ (100 mL) was added to the residue. The solution was filtered through a short silica gel pad. The pad was washed with CH$_2$Cl$_2$ (150 mL). The filtrate was combined and the solvent removed under vacuum to give the product as a white colourless solid. Yield=12.4 g (97.9%). $^1$H NMR (300 MHz, CDCl$_3$) δ: 7.17-7.14 (m, 8H), 6.27-6.25 (m, 4H), 3.63 (s, 6H), 3.62 (s, 6H), 3.59 (s, 6H), 3.07 (s, 6H), 1.30 (s, 36H), 1.29 (s, 36H). $^{31}$P NMR (121.1 MHz, CDCl$_3$) δ: −13.75.

f) Preparation of (S)-(4,4',6,6'-tetramethoxybiphenyl-2,2'-diyl)bis(bis(3,5-di-tert-butyl-4-methoxyphenyl)phosphine)

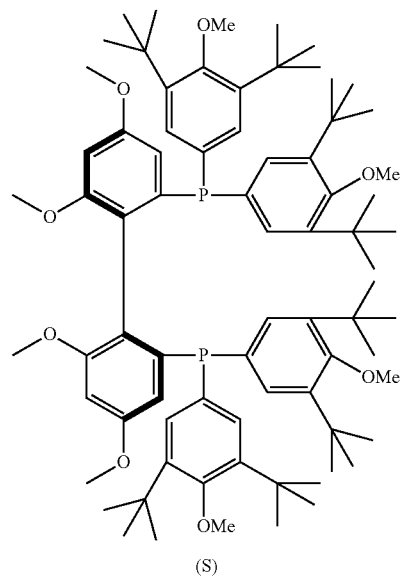

(S)

(S)-(4,4',6,6'-tetramethoxybiphenyl-2,2'-diyl)bis(bis(3,5-di-tert-butyl-4-methoxyphenyl)phosphine) was prepared from (S)-(4,4',6,6'-tetramethoxybiphenyl-2,2'-diyl)bis(bis(3,5-di-tert-butyl-4-methoxyphenyl)-phosphine) oxide using the procedure outlined above.

Example 42

Preparation of PtCl$_2$((R)-Ph-Garphos)

In an argon-filled flask, PtCl$_2$(COD) (0.075 g, 0.20 mmol) and (R)-Ph-Garphos (0.129 g, 0.20 mmol) were combined. Methylene chloride (2 mL) was added to the flask and the resulting pale yellow solution was left to stir for approximately 2 hours. The solution was then reduced to dryness in vacuo leaving a pale yellow residue. Yield: 0.153 g (93%). $^1$H NMR (300 MHz, CD$_2$Cl$_2$): δ 7.85 (br m, 4H, Ar), 7.73 (br m, 4H, Ar) 7.55-7.25 (br m, 12H, Ar), 6.23 (br m, 2H, Ar), 5.92 (m, 2H, Ar), 3.49 (s, 6H, MeO—), 3.47 (s, 6H, MeO—). $^{31}$P NMR (121 MHz, CD$_2$Cl$_2$): δ 9.85 (s, J$_{Pt-P}$=3640 Hz).

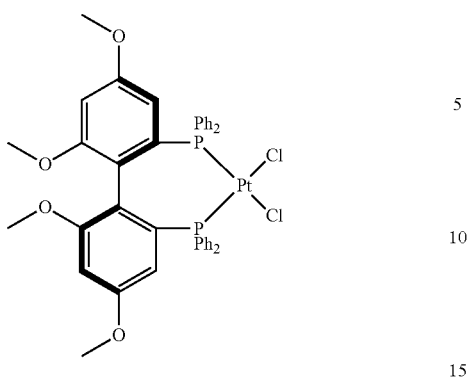

Example 43

Preparation of Pd(OAc)₂((R)-Ph-Garphos)

In an argon-filled flask, Pd(OAc)₂ (0.050 g, 0.22 mmol) and (R)-Ph-Garphos (0.143 g, 0.22 mmol) were combined. Methylene chloride (2 mL) was added to the flask and the resulting orange/brown solution was left to stir for approximately 2 hours. The solution was then reduced to dryness in vacuo leaving an orange residue. Yield: 0.171 g (89%). $^1$H NMR (300 MHz, CD₂Cl₂): δ 8.00 (br m, 4H, Ar), 7.75 (br m, 4H, Ar) 7.48-7.30 (br m, 12H, Ar), 6.28 (br m, 2H, Ar), 5.88 (m, 2H, Ar), 3.55 (s, 6H, MeO—), 3.36 (s, 6H, MeO—), 1.25 (br s, 6H, —OAc). $^{31}$P NMR (121 MHz, CD₂Cl₂): δ 26.4 (s).

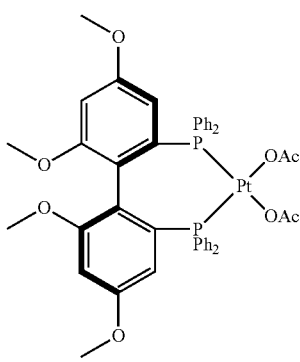

Example 44

Preparation Pd(acac)₂((R)-Ph-Garphos)

In an argon-filled flask, Pd(acac)₂ (0.075 g, 0.25 mmol) and (R)-Ph-Garphos (0.158 g, 0.25 mmol) were combined. Methylene chloride (2 mL) was added to the flask and the resulting yellow/brown solution was left to stir for approximately 2 hours. The solution was then reduced to dryness in vacuo leaving a yellow/orange residue. Yield: 0.224 g (96%). $^1$H NMR (300 MHz, CD₂Cl₂): δ 7.75 (br m, 4H, Ar), 7.33-7.60 (br m, 16H, Ar), 6.28 (br m, 2H, Ar), 6.06 (m, 2H, Ar), 5.43 (s, acac-H), 3.56 (s, 6H, MeO—), 3.51 (s, 6H, MeO—), 2.08 (s, 6H, acac-Me), 1.49 (s, 6H, acac-Me). $^{31}$P NMR (121 MHz, CD₂Cl₂): δ 31.7 (s).

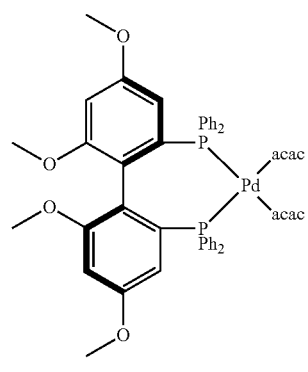

Example 45

General Procedure for Suzuki-Miyaura Coupling

To a solution of bromobenzene (0.079 g, 0.5 mmol), phenyl boronic acid (0.073 g, 0.60 mmol) and potassium carbonate (0.138 g, 1 mmol) in 1,4-dioxane solvent (2.0 mL) was added the solid catalyst (0.01 mmol, 2 mol %) under argon gas. The reaction was then stirred at 80° C. for 16 hours. The mixture was then cooled to room temperature, filtered and concentrated in vacuo. The residue was subsequently purified by silica gel chromatography (hexanes/EtOAc or hexanes/ether). The isolated product was characterized by $^1$H NMR spectroscopy. Characterization Data (Biphenyl): Isolated as colorless solid; $^1$H NMR (CDCl₃, 300 MHz): δ 7.71 (4H, d, J=7.8 Hz), 7.55 (4H, t, J=7.5 Hz), 7.45 (2H, t, J=7.2 Hz). Results are shown in Table 4.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Hydrogenation of ethyl 4-chloroacetoacetate using RuCl₂(p-cymene)-(R—Ph-Garphos)

| Entry | Temp. (0° C.) | Solvent | S/C | Time (h) | Conv. (%) | Yield (%) | e.e. (%) |
|---|---|---|---|---|---|---|---|
| 1 | 100 | EtOH/CH₂Cl₂ = 2.5 | 10,000 | 1 | >99 | 93.9 | 95.2 |
| 2 | 110 | EtOH/CH₂Cl₂ = 2.5 | 10,000 | 1 | >99 | 93.5 | 95.4 |
| 3 | 120 | EtOH/CH₂Cl₂ = 2.5 | 10,000 | 1 | >99 | 91.2 | 96 |
| 4 | 110 | EtOH/CH₂Cl₂ = 3 | 50,000 | 2 | >99 | 92 | 94 |

TABLE 1-continued

Hydrogenation of ethyl 4-chloroacetoacetate using RuCl₂(p-cymene)-(R—Ph-Garphos)

| Entry | Temp. (0° C.) | Solvent | S/C | Time (h) | Conv. (%) | Yield (%) | e.e. (%) |
|---|---|---|---|---|---|---|---|
| 6 | 120 | EtOH/CH₂Cl₂ = 3 | 100,000 | 2 | >99 | 88 | 94.5 |
| 8 | 100 | EtOH/CH₂Cl₂ = 20 | 10,000 | 1 | >99 | 90.5 | 97.6 |
| 9 | 120 | EtOH/CH₂Cl₂ = 20 | 10,000 | 1 | >99 | 91.8 | 97.1 |
| 10 | 110 | EtOH/CH₂Cl₂ = 20 | 10,000 | 1 | >99 | 91.8 | 96 |
| 11 | 90 | EtOH/CH₂Cl₂ = 20 | 10,000 | 1 | >99 | 94.6 | 96.6 |
| 12 | 80 | EtOH/CH₂Cl₂ = 20 | 10,000 | 1 | 73 | 66.3 | 90.5 |
| 13 | 120 | EtOH/CH₂Cl₂ = 30 | 50,000 | 2.5 | >99 | 88 | 94.8 |
| 14 | 110 | EtOH/CH₂Cl₂ = 30 | 50,000 | 3 | 98.5 | 83 | 92.5 |
| 15 | 100 | EtOH/CH₂Cl₂ = 30 | 50,000 | 3 | >99 | 88 | 92.8 |
| 16 | 120 | EtOH/CH₂Cl₂ = 20 | 100,000 | 3 | 98.2 | 82.4 | 96.5 |
| 17 | 110 | EtOH/CH₂Cl₂ = 20 | 100,000 | 4 | 96 | 75.3 | 95 |

TABLE 2

Hydrogenation of simple ketones using RuCl₂(Garphos)(Diamine) as catalyst (H₂ = 10 atm).

| entry | Cat. | ketone | S/C/B | Temp. (° C.) | Time (h) | Conv. (%) | e.e (%) |
|---|---|---|---|---|---|---|---|
| 1 | RuCl₂((S)—Ph-Garphos)(S,S—DPEN) | acetophenone | 1000/1/10 | 25 | 3 | >99 | 90 (R) |
| 2 | RuCl₂((R)-Xylyl-Garphos)(R,R—DPEN) | acetophenone | 1000/1/15 | 25 | 3 | >99 | 98.6 (S) |
| 3 | RuCl₂((R)—DMM-Garphos)(R,R—DPEN) | acetophenone | 1000/1/15 | 25 | 1.5 | >99 | 98.5 (S) |
| 4 | RuCl₂((S)-Xylyl-Garphos)(S-DAIPEN) | acetophenone | 5000/1/75 | 25 | 3 | >99 | 99.3 (R) |
| 5 | RuCl₂((R)—DMM-Garphos)(R,R-DAIPEN) | acetophenone | 1000/1/15 | 25 | 1.5 | >99 | 99.4 (S) |
| 6 | RuCl₂((S)-Xylyl-Garphos)(S-DAIPEN) | 3'-(trifluoromethyl)acetophenone | 5000/1/15 | 25 | 3 | >99 | 99.5 (R) |

TABLE 2-continued

Hydrogenation of simple ketones using RuCl$_2$(Garphos)(Diamine) as catalyst (H$_2$ = 10 atm).

| entry | Cat. | ketone | S/C/B | Temp. (°C.) | Time (h) | Conv. (%) | e.e (%) |
|---|---|---|---|---|---|---|---|
| 7 | RuCl$_2$((S)-Xylyl-Garphos) (S-DAIPEN) | 2'-fluoroacetophenone | 5000/1/15 | 25 | 4 | >99 | 97 (R) |
| 8 | RuCl$_2$((S)-Xylyl-Garphos) (S-DAIPEN) | 4'-fluoroacetophenone | 5000/1/15 | 25 | 3 | >99 | 99.5 (R) |
| 9 | RuCl$_2$((S)-Xylyl-Garphos) (S-DAIPEN) | propiophenone | 5000/1/15 | 25 | 3.5 | >99 | >99.9 (R) |
| 10 | RuCl$_2$((S)-Xylyl-Garphos) (S-DAIPEN) | 1-(3,5-bis(trifluoromethyl)phenyl)ethanone | 1000/1/15 | 25 | 1.5 | 100 | 99.7 (R) |
| 11 | RuCl$_2$((S)-Xylyl-Garphos) (S-DAIPEN) | " | 100,000/1/1500 | 25 | 24 | 99.6 | 99.4 (R) |
| 12 | RuCl$_2$((S)-Xylyl-Garphos) (S-DAIPEN) | 3-(dimethylamino)-1-(thiophen-2-yl)propan-1-one | 2000/1/8 | 25 | 20 | Yield: 60% | 99.2 |

TABLE 3

Hydrogenation of 1-(3,5-bis(trifluoromethyl)phenyl)ethanone using RuCl$_2$(Garphos)(Diamine) as catalyst 3,5-(CF$_3$)$_2$C$_6$H$_3$-CO-CH$_3$ + H$_2$ $\xrightarrow{\text{Cat/KO}^t\text{Bu}}_{\text{i-PrOH, P}_{H2} = 160 \text{ Psi}}$ 3,5-(CF$_3$)$_2$C$_6$H$_3$-CH(OH)-CH$_3$

| Entry | catalyst | S/C/B | Time(h) | Conv.(%) | e.e. (%) |
|---|---|---|---|---|---|
| 1 | RuCl$_2$((S)—Ph-Garphos) (S,S—DPEN) | 1000:1:10 | 3 | 100 | 70 |
| 2 | RuCl$_2$((R)-Xylyl-Garphos) (R,R—DPEN) | 1000:1:15 | 2 | 100 | 96 |
| 3 | RuCl$_2$((S)-Xylyl-Garphos) (S-DAIPEN) | 1000:1:15 | 1.5 | 100 | 99.6 |
| 4 | RuCl$_2$((S)-Xylyl-Garphos) (S-DAIPEN) | 1000:1:15 | 1.5 | 100 | 99.7 |
| 5 | RuCl$_2$((S)-Xylyl-Garphos) (S-DAIPEN) | 5000:1:75 | 0.5 | 100 | 99.4 |

TABLE 3-continued

Hydrogenation of 1-(3,5-bis(trifluoromethyl)phenyl)ethanone using RuCl$_2$(Garphos)(Diamine) as catalyst

| Entry | catalyst | S/C/B | Time(h) | Conv.(%) | e.e. (%) |
|---|---|---|---|---|---|
| 6 | RuCl$_2$((S)-Xylyl-Garphos) (S-DAIPEN) | 10,000:1:150 | 1 | 100 | 99.5 |
| 7 | RuCl$_2$((S)-Xylyl-Garphos) (S-DAIPEN) | 50,000:1:750 | 6 | 100 | 99.5 |
| 8 | RuCl$_2$((S)-Xylyl-Garphos) (S-DAIPEN) | 100,000:1:1500 | 24 | 99.6 | 99.4 |

TABLE 4

Suzuki-Miyaura Coupling for the Production of Phenylbenzene using Pd(Garphos)(OAc)$_2$ or Pd(Garphos)(acac)$_2$

| Entry | Catalyst | % Yield |
|---|---|---|
| 1 | Pd(OAc)$_2$((R)—Ph-Garphos) | 84.7 |
| 2 | Pd(acac)$_2$((R)—Ph-Garphos) | 99.6 |

We claim:

1. A compound of the Formula (B):

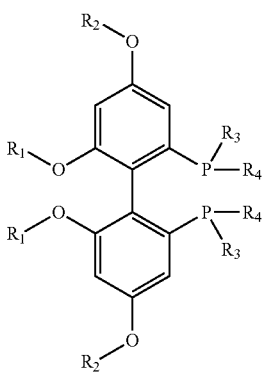

(B)

wherein R$_1$ and R$_2$ are independently or simultaneously C$_{1-20}$-(alkyl), C$_{2-20}$-(alkenyl), C$_{2-20}$-(alkynyl), C$_{3-20}$-(cycloalkyl) or C$_{6-14}$-(aryl), all of which are optionally substituted, R$_3$ and R$_4$ are independently or simultaneously C$_{1-20}$-(alkyl), C$_{2-20}$-(alkenyl), C$_{2-20}$-(alkynyl), C$_{3-20}$-(cycloalkyl), C$_{6-14}$-(aryl), C$_{5-14}$-(heteroaryl)-O—C$_{1-20}$-(alkyl), (aryl), —O—CH$_2$—C$_{6-14}$-(aryl), all of which are optionally substituted, or R$^3$ and R$^4$ are linked together to form an optionally substituted monocyclic or polycylic ring system having 4 or more atoms, including the phosphorous atom to which said groups are bonded, and in which one or more carbon atoms in said monocyclic or polycyclic ring system is optionally replaced with a heteromoiety selected from O, S, N, NR$^5$, SiR$^5$ and SiR$^5$R$^6$, the optional substituents are selected from one or more of halo, OR$^5$, NR$^5$R$^6$ and R$^7$, R$^5$ and R$^6$ are simultaneously or independently H, fluoro-substituted-C$_{1-6}$alkyl, C$_{1-6}$ alkyl, C$_{2-6}$alkenyl, C$_{2-6}$alkynyl or C$_{6-14}$aryl, and R$^7$ is fluoro-substituted-C$_{1-6}$alkyl, C$_{1-6}$alkyl, C$_{2-6}$alkenyl, C$_{2-6}$alkynyl, or C$_{6-14}$aryl.

2. The compound according to claim 1, wherein R$_1$ and R$_2$ are independently or simultaneously C$_{1-10}$-(alkyl), C$_{2-10}$-(alkenyl), C$_{2-10}$-(alkynyl), C$_{3-10}$-(cycloalkyl) or C$_{6-10}$-(aryl), all of which are optionally substituted.

3. The compound according to claim 2, wherein R$_1$ and R$_2$ are independently or simultaneously C$_{1-6}$-(alkyl), C$_{2-6}$-(alkenyl), C$_{2-6}$-(alkynyl), C$_{3-6}$-(cycloalkyl) or phenyl, all of which are optionally substituted.

4. The compound according to claim 3, wherein R$_1$ and R$_2$ are independently or simultaneously methyl, ethyl, propyl, butyl or phenyl, all of which are optionally substituted.

5. The compound according to claim 4, wherein R$_1$ and R$_2$ are independently or simultaneously methyl, ethyl or propyl, all of which are optionally substituted.

6. The compound according to claim 5, wherein R$_1$ and R$_2$ are simultaneously methyl.

7. The compound according to claim 1, wherein R$_3$ and R$_4$ are independently or simultaneously C$_{1-10}$-(alkyl), C$_{2-10}$-(alkenyl), C$_{2-10}$-(alkynyl), C$_{3-10}$-(cycloalkyl), C$_{6-10}$-(aryl), C$_{5-10}$(heteroaryl)-O—C$_{1-10}$-(alkyl), —O—C$_{6-10}$-(aryl), —O—CH$_2$—C$_{6-10}$-(aryl), all of which are optionally substituted.

8. The compound according to claim 7, wherein $R_3$ and $R_4$ are independently or simultaneously $C_{1-6}$-(alkyl), $C_{2-6}$-(alkenyl), $C_{2-6}$-(alkynyl), $C_{3-6}$-(cycloalkyl), phenyl, $C_{5-6}$-(heteroaryl)-O—$C_{1-6}$-(alkyl), —O-phenyl, —O—$CH_2$-phenyl, all of which are optionally substituted.

9. The compound according to claim 8, wherein $R_3$ and $R_4$ are independently or simultaneously phenyl, tolyl (4-methylphenyl), anisyl (4-methoxyphenyl), xylyl (3,5-dimethylphenyl), 3,5-dimethyl-4-methoxy-phenyl, 3,5-di-tert-butyl-4-methoxy-phenyl or 3,5-bis(trifluoromethyl)-phenyl, all of which are optionally substituted.

10. The compound according to claim 1, wherein $R^3$ and $R^4$ are linked together to form an optionally substituted monocyclic or bicyclic, saturated, unsaturated and/or aromatic ring system having 4 to 14 atoms, including the phosphorous atom to which said groups are bonded, and in which one or more carbon atoms in said monocyclic or bicyclic ring system is optionally replaced with a heteromoiety selected from O, S, N, NH and $NC_{1-4}$alkyl.

11. The compound according to claim 10, wherein $R^3$ and $R^4$ are linked together to form an optionally substituted monocyclic or bicyclic, saturated, unsaturated and/or aromatic ring system having 4 to 10 atoms, including the phosphorous atom to which said groups are bonded.

12. The compound according to claim 1, wherein the optional substituents are one or more of halo, OH, $NH_2$, $NHR^5$, $OR^5$, $NR^5R^6$ and $R^7$, in which $R^5$, $R^6$ and $R^7$ are simultaneously or independently selected from fluoro-substituted-$C_{1-4}$alkyl, $C_{1-4}$alkyl, $C_{2-4}$alkenyl, phenyl and $C_{1-4}$alkylenephenyl.

13. The compound according to claim 12, wherein $R^5$, $R^6$ and $R^7$ are simultaneously or independently selected from methyl, benzyl and phenyl.

14. A metal complex containing a compound of formula (B), wherein the compound of the formula (B) is as claimed in claim 1.

15. A metal complex having the formula [RuX$_2$(ligand) (B)], wherein X is halo and ligand is any neutral ligand, wherein the compound of the formula (B) is as claimed in claim 1.

16. The metal complex according to claim 15, wherein the neutral ligand is p-cymene, 1,5-cyclooctadiene (COD) or diamine.

17. The metal complex according to claim 16, wherein the metal complex is RuCl$_2$((S)-Ph-Garphos)(S,S-DPEN), RuCl$_2$((S)-Ph-Garphos)(S)-DAIPEN), RuCl$_2$((S)-Xylyl-Garphos)(S,S-DPEN), RuCl$_2$((S)-Xylyl-Garphos)(S)-DAIPEN), RuCl$_2$((S)-DMM-Garphos)(S,S-DPEN) or RuCl$_2$((S)-DMM-Garphos)((S)-DAIPEN), wherein (i) Ph-Garphos has the structure,

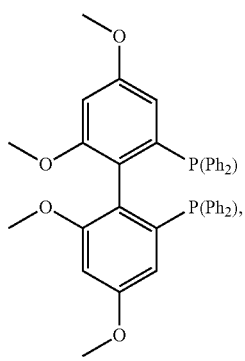

(ii) Xylyl-Garphos has the structure,

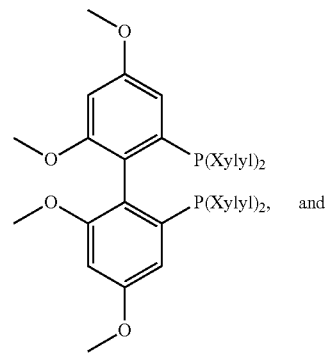

and (iii) DMM-Garphos has the structure

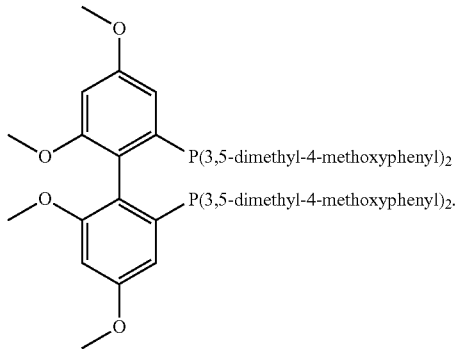

18. A metal complex having the formula [Rh(ligand)(B)] [X], wherein ligand is any neutral ligand and X is any anionic ligand, wherein the compound of the formula (B) is as claimed in claim 1.

19. The metal complex according to claim 18, wherein the metal complex is [Rh(COD)((R)-Ph-Garphos)][BF$_4$], [Rh (COD)((R)-Xylyl-Garphos)][BF$_4$] or [Rh(COD)((R)-DMM-Garphos)][BF$_4$], wherein COD is 1,5-cyclooctadiene, and (i) Ph-Garphos has the structure,

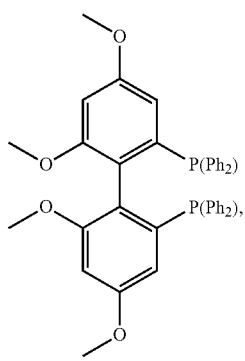

(ii) Xylyl-Garphos has the structure,
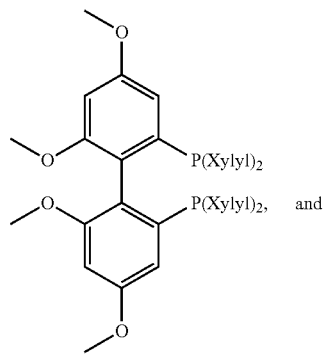
(iii) DMM-Garphos has the structure
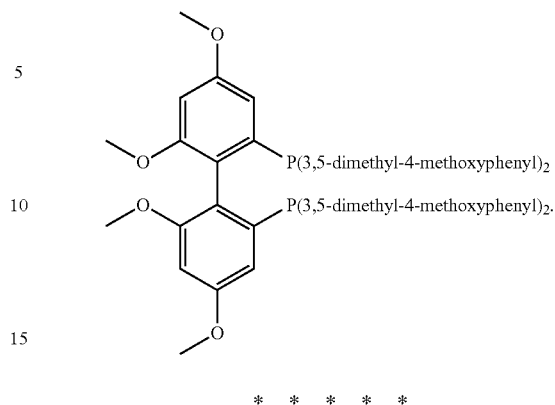
* * * * *

UNITED STATES PATENT AND TRADEMARK OFFICE
CERTIFICATE OF CORRECTION

PATENT NO. : 9,062,085 B2
APPLICATION NO. : 13/821290
DATED : June 23, 2015
INVENTOR(S) : Kamaluddin Abdur-Rashid et al.

It is certified that error appears in the above-identified patent and that said Letters Patent is hereby corrected as shown below:

In the Claims,

Column 53, line 42, the image of Claim 1 should read "(B)" positioned just to the bottom right of said image.

Column 53, line 62, Claim 1 should read "... C1-20-(alkyl), -O-C6-14-(aryl), -O-CH2-C6-14-(aryl)...".

Column 56, line 12, Claim 17 should read ", and" after the image for the chemical "xylyl-garphos" rather than being incorporated into the image.

Column 58, line 11, Claim 19 should read ", and" after the image for the chemical "xylyl-garphos" rather than being incorporated into the image.

Signed and Sealed this
Twentieth Day of October, 2015

Michelle K. Lee
*Director of the United States Patent and Trademark Office*